United States Patent [19]

Pohjala et al.

[11] Patent Number: 5,376,649
[45] Date of Patent: Dec. 27, 1994

[54] PARTIAL ESTERS OF (DI) CHLOROMETHANEDIPHOSPHONIC ACID USEFUL FOR TREATING DISORDERS RELATING TO THE METABOLISM OF CALCIUM

[75] Inventors: Esko Pohjala, Tampere; Keikki Nupponen, Kangasala; Jouko Vepsäläinen, Tampere, all of Finland

[73] Assignee: Leiras Oy, Turku, Finland

[21] Appl. No.: 777,555

[22] PCT Filed: Jun. 19, 1990

[86] PCT No.: PCT/FI90/00163

§ 371 Date: Feb. 3, 1992

§ 102(e) Date: Feb. 3, 1992

[87] PCT Pub. No.: WO90/15806

PCT Pub. Date: Dec. 27, 1990

[30] Foreign Application Priority Data

Jun. 21, 1989 [FI] Finland .................. 893039

[51] Int. Cl.$^5$ .................. A61K 31/66; C07F 9/40
[52] U.S. Cl. .................. 514/108; 558/155; 558/161
[58] Field of Search .................. 558/155, 161; 514/108

[56] References Cited

U.S. PATENT DOCUMENTS

| | | |
|---|---|---|
| 3,303,139 | 2/1967 | Blaser et al. |
| 3,683,080 | 8/1972 | Francis .................. 514/107 |
| 3,957,858 | 5/1976 | Kerst . |
| 3,962,318 | 6/1976 | Kerst . |
| 4,234,645 | 11/1980 | Gunther et al. .................. 514/108 |
| 4,634,691 | 1/1987 | Hedglin et al. .................. 514/108 |
| 4,732,998 | 3/1988 | Binderup .................. 558/161 |

FOREIGN PATENT DOCUMENTS

| | | |
|---|---|---|
| 0186405 | 7/1986 | European Pat. Off. . |
| 0356866 | 3/1990 | European Pat. Off. . |
| 1617118 | 2/1971 | Germany . |
| 1201984 | 9/1968 | United Kingdom . |

OTHER PUBLICATIONS

*Organic Phosphorus Compounds;* Kosolapoff, G. M. et al. Eds.; vol. 7; Wiley–Interscience: New York, 1976; pp. 9–10.

Chem. Abstracts, vol. 111, No. 19, 6 (Nov. 1989), p. 748, abstract 174388h and JP,A,63295595 (Yamanouchi Pharmaceutical Co., Dec. 1, 1988).

Chem. Abstracts, vol. 92, No. 7, 18 (Feb. 1980) p. 27, abstract 51765k and Probl.Gematol. Perelir. Kvori, 1979, 24(8), 14–17 (Russ).

*Primary Examiner*—Mary C. Lee
*Assistant Examiner*—Michael G. Ambrose
*Attorney, Agent, or Firm*—Wolf, Greenfield and Sacks

[57] ABSTRACT

Novel pharmaceutically active bisphosphonic acid derivatives of formula (I), in which $R^1$, $R^2$, $R^3$ and $R^4$ independently are $C_1$–$C_{22}$-alkyl, $C_2$–$C_{22}$-alkenyl, $C_2$–$C_{22}$-alkynyl, $C_3$–$C_{10}$-cycloalkyl, $C_3$–$C_{10}$-cycloalkenyl, aryl, aralkyl, silyl and hydrogen, and $R^4$ is different from hydrogen, $Q^1$ is hydrogen, fluorine, chlorine, bromine or iodine, and $Q^2$ is chlorine, bromine or iodine, including the stereoisomers, such as the geometrical isomers and optically active isomers, of the compounds, as well as the pharmaceutically acceptable salts of the compounds.

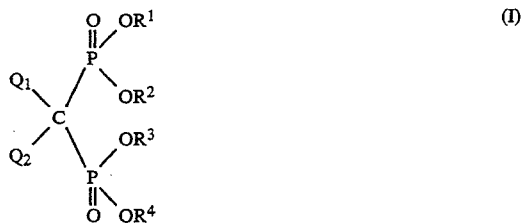

6 Claims, No Drawings

PARTIAL ESTERS OF (DI) CHLOROMETHANEDIPHOSPHONIC ACID USEFUL FOR TREATING DISORDERS RELATING TO THE METABOLISM OF CALCIUM

BACKGROUND OF THE INVENTION

The invention concerns novel methylenebisphosphonic acid derivatives, in particular novel halogen substituted methylenebisphosphonic ester acids and ester salts, as well as processes for the preparation of these novel compounds and pharmaceutical compositions comprising such novel compounds.

Several publications disclose methylenebisphosphonic acids, their salts or some tetraesters, but there are only a few disclosures of corresponding halogen substituted tri-, di- and monoesters (partial esters). The U.S. Pat. No. 4,478,763 (1984) discloses a new process for the preparation of unsymmetrical isopropyl esters of (mono- and difluoromethylene)bisphosphonic acids. As further publications disclosing fluorine substituted compounds, the following may be mentioned: J. Org. Chem., 51, (1986), 4788, J. Am. Chem. Soc., (1987) 5542, and Bioorg. Chem., (1988) 111. Thus neither the properties of the novel partial esters of (halogenmethylene)bisphosphonic acids and their salts according to the invention, nor their use as medicaments, have been investigated.

SUMMARY OF THE INVENTION

According to the invention it has now been discovered that the novel partial esters of methylenebisphosphonic acids and their salts in many cases exhibit more favourable properties than the corresponding bisphosphonic acids and their salts due to their better kinetics and availability and, their ability to participate as complex formers in the regulation of the metabolism of the organism being maintained.

In addition they are well suited for the treatment of disorders relating to the metabolism of calcium and of other, especially bivalent metals. They may be used for the treatment of diseases in the skeletal system, especially of bone formation and resorption disorders, such as of osteoporosis and Paget's disease, as well as for the treatment of diseases in the soft tissues, such as of deposition and mineralization conditions and bone formation disorders.

DETAILED DESCRIPTION

The novel bisphosphonates regulate either directly or by an indirect mechanism the level of cations freely present in the body fluids, as well as the level of cations binding to, active in and liberated from the tissues. Thus they are able to regulate the cellular metabolism, growth and destruction. Consequently they are useful for the treatment of e.g. cancer of the bone and metastases thereof, ectopic calcifications, urolithiasis, rheumatoid arthritis, bone infections and bone degradation.

The invention concerns novel methylenebisphosphonic acid derivatives of the general formula I

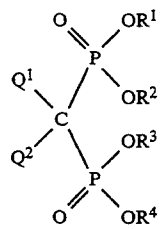

in which formula $R^1$, $R^2$, $R^3$ and $R^4$ independently are $C_1$–$C_{22}$-alkyl, $C_2$–$C_{22}$-alkenyl, $C_2$–$C_{22}$-alkynyl, $C_3$–$C_{10}$-cycloalkyl, $C_3$–$C_{10}$-cycloalkenyl, aryl, aralkyl, silyl or hydrogen, whereby in the formula I at least one of the groups $R^1$, $R^2$, $R^3$ and $R^4$ is hydrogen and at least one of the groups $R^1$, $R^2$, $R^3$ and $R^4$ is different from hydrogen, $Q^1$ is hydrogen, fluorine, chlorine, bromine or iodine, and $Q^2$ is chlorine, bromine or iodine, including the stereoisomers, such as the geometrical isomers and the optically active isomers, of the compounds, as well as the pharmaceutically acceptable salts of the compounds.

$C_1$–$C_{22}$-alkyl is straight or branched, preferably lower alkyl with 1 to 7 C-atoms, preferably 1 to 4 C-atoms, such as methyl, ethyl, propyl, isopropyl, or butyl, i-butyl, s-butyl or t-butyl, or pentyl, hexyl or heptyl, whereby preferably at least two, but more preferably three of the groups $R^1$, $R^2$, $R^3$ and $R^4$ are hydrogen or it is $C_8$–$C_{22}$-alkyl, whereby preferably at least two, but more preferably three of the groups $R^1$, $R^2$, $R^3$ and $R^4$ are hydrogen. Long chain is preferably a straight or branched $C_{14}$–$C_{18}$-alkyl group.

$C_2$–$C_{22}$-alkenyl may also be straight or branched, and is preferably lower alkenyl with 2 to 7 C-atoms, preferably 2 to 4 C-atoms, and has the meaning of ethenyl, 1-methyl-ethenyl, 1-propenyl, allyl or butenyl, 2-methyl-2-propenyl or also pentenyl, isopentenyl, 3-methyl-2-butenyl, hexenyl or heptenyl, whereby preferably at least two, but more preferably three of the groups $R^1$, $R^2$, $R^3$ and $R^4$ are hydrogen, or it is $C_8$–$C_{22}$-alkenyl, whereby preferably at least two, but more preferably three of the groups $R^1$, $R^2$, $R^3$ and $R^4$ are hydrogen. Higher alkenyl is preferably a straight or branched $C_{14}$–$C_{18}$-alkenyl group. The said alkenyl groups may be either in E- or Z-form, or they may be conjugated or unconjugated dienyls, such as 3,7-dimethyl-2,6-octadiene, trienyls, such as farnesyl or polyenyls.

$C_2$–$C_{22}$-alkynyl may also be straight or branched, and is preferably lower alkynyl with 2 to 7 C-atoms, preferably 2 to 4 C-atoms, and means ethynyl, 1-propynyl, propargyl, or butynyl, or also pentynyl, hexynyl or heptynyl, whereby preferably at least two, but more preferably three of the groups $R^1$, $R^2$ $R^3$ and $R^4$ are hydrogen, or it is also $C_8$–$C_{22}$-alkynyl, whereby preferably at least two, but more preferably three of the groups $R^1$, $R^2$, $R^3$ and $R^4$ are hydrogen. Higher alkynyl is preferably a straight or branched $C_{14}$–$C_{18}$-alkynyl group. Also conjugated or unconjugated di-, tri- and poly-ynyl and alkenynyl groups may be used.

Cycloalkyl and -alkenyl contain 3 to 10 C-atoms and they may be substituted or unsubstituted, especially mono- or bicyclic, being preferably unsubstituted cyclopropyl, -butyl, -pentyl, -hexyl or -heptyl or bicyclo[3.2.0]- or -[2.2.1]heptyl, -[4.2.0]- or [3.2.1]octyl, -[3.3.1]nonyl, or the corresponding spiro-hydrocarbon residue, as well as the corresponding cycloalkenyl group or unsaturated spiro structure, or it may be polycyclic, such as adamantyl.

As possible substituents, both in cis- and trans-isomers, for example $C_1$–$C_4$-alkyl and -alkenyl may be used.

Aryl means a substituted or unsubstituted carbocyclic aromatic ring, such as phenyl, or a poly-, especially bicyclic, conjugated or bridged unsaturated or partly saturated ring system, such as naphtyl, phenanthryl, indenyl, indanyl, tetrahydronaphtyl, biphenyl, di- and triphenylmethyl etc.

Aralkyl may be illustrated by the following formula

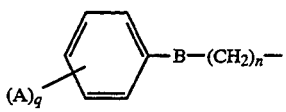

wherein the groups A mean independently $C_1$–$C_4$-alkyl, $C_1$–$C_4$-alkoxy, halogen or nitro, q is an integer from 0 to 3, n is an integer from 0 to 6, and B is a straight or branched $C_1$–$C_6$-alkyl group or a conjugated or unconjugated $C_2$–$C_6$-alkenyl or -alkynyl group.

In the silyl group ($SiR_3$) the group R is lower alkyl containing 1 to 4 C-atoms, and is especially methyl, ethyl, isopropyl, butyl, t-butyl, or it is phenyl or R-substituted phenyl, whereby also different combinations of lower alkyl and phenyl groups may be used, such as in dimethyl t-butyl-, methyl di-isopropyl-, dimethyl- and diethyl phenyl-, methyl t-butyl phenyl-, di-isopropyl- ( 2,6-dimethyl phenyl ) -, and- ( 2,4,6-tri-isopropyl phenyl)silyl.

The salts of the compounds of the formula I are especially their salts with pharmaceutically acceptable bases, such as metal salts, for example alkalimetal salts, especially litium, sodium and potassium salts, alkaline earth metal salts, such as calcium or magnesium salts, copper, aluminium or zinc salts, as well as ammonium salts with ammonia or with primary, secondary and tertiary, both aliphatic and alicyclic and aromatic amines, as well as quaternary ammonium salts, such as halides, sulphates and hydroxides, salts with aminoalcohols, such as ethanol-, diethanol- and triethanolamines, tris(hydroxymethyl)aminomethane, 1- and 2-methyl and 1,1-, 1,2- and 2,2-dimethylaminoethanols, N-mono- and N,N-dialkylaminoethanols, N-(hydroxymethyl- and ethyl)-N,N-ethanediamines, as well as amino crown ethers and cryptates, and heterocyclic ammonium salts, such as azetidinium, pyrrolidinium, piperidinium, piperazinium, morpholinium, pyrrolium, imidazolium, pyridinium, pyrimidinium, quinolinium, etc., salts.

An advantageous subgroup of the compounds of the formula I comprises the mono-, di- and triesters of the formula I, wherein $Q^1=Q^2=$ chlorine, and $R^1$ to $R^4$ are lower alkyl, especially methyl and ethyl. Another advantageous subgroup comprises the compounds of the formula I, wherein $Q^1=Q^2=$ chlorine and one or two of the groups $R^1$ to $R^4$ are $C_{14}$–$C_{18}$-alkyl or -alkenyl.

Especially advantageous compounds according to the invention are the monomethyl- and monoethylesters of (dichloro-, fluorochloro-, bromochloro-, and dibromomethylene)bisphosphonic acids.

An especially advantageous compound is the monomethyl- and monoethylester of (dichloromethylene)bisphosphonic acid.

The invention concerns also a process for the preparation of the compounds of the formula I.

According to one process the compounds are prepared by selective hydrolysis of the tetraesters corresponding to the formula I. Thus a tetraester II is used as the starting material, wherein the groups $R^1$–$R^4$ (not hydrogen) and $Q^1$ and $Q^2$ have the same meaning as in the formula I and this tetraester is hydrolyzed stepwise according to the following Scheme 1 to the triester III, diester IV and v and the monoester VI (the reaction S takes place in the direction of the upper arrow). If necessary, the partial ester III to VI or its salt may be isolated and purified by extraction, fractional crystallization or chromatographically, and if desired, a free acid may be converted into a salt or a salt into the free acid.

Scheme 1

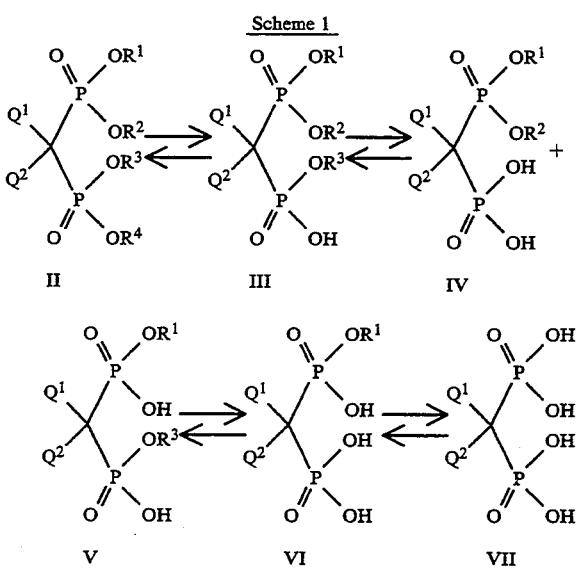

The hydrolysis of the tetraesters of the formula II may be carried out by treating with both an acid and a base, using thermal cleaving, and in certain cases also using water, an alcohol, an amide or other neutral or nonneutral transalkylation, -silylation and -arylation reagents. The hydrolysis takes place advantageously at a temperature range of 20° to 150° C., generally from about 50° C. to the boiling point of the mixture. The acids are advantageously conventional inorganic acids, such as hydrochloric acid, sulphuric acid, phosphoric acid, and Lewis acids, such as borotrifluoride etherate, titanium tetrachloride, etc., as well as a number of organic acids, such as oxalic acid, formic acid, acetic acid and other carboxylic acids, methanesulphonic acid and other sulphonic acids, such as P-toluene sulphonic acid, further chlorine and fluorine substituted carboxylic and sulphonic acids, such as trichloroacetic acid and trifluoromethane sulphonic acid, and their aqueous solutions.

The bases are advantageously alkali and ammonium-hydroxides and ammonia and the aqueous solutions thereof, as well as a number of amines, such as primary, secondary and tertiary amines, such as diethyl, triethyl, diisopropyl and tributyl amine, aniline, and N- and N,N-alkyl substituted anilines and heterocyclic amines, such as pyridine, morpholine, piperidine, piperazine etc., and hydrazines, such as N,N-dimethyl hydrazine.

In addition, acids and bases bound to a solid substrate may be used, such as Amberlites, either in the presence of an organic solvent or water or various solvent mixtures, or in the absence thereof.

Further by treating with certain alkalimetals, such as sodium and litium, or with suitable inorganic salts, such as with sodium iodide, litium bromide, ammonium chloride and NaBr/PTC, the ester group may be converted directly to its corresponding salt, such as to the sodium, ammonium and litium phosphonates.

Thermal cleaving usually takes place at a temperature of about 100° to 400° C., usually, however, at a temperature of not more than 250° C. The presence of a suitable catalyst, such as an acid or an acid solution, or a quaternary ammonium salt, makes it possible to perform the reaction faster and at a lower temperature. Some active substituents, such as benzyl and allyl, may be removed by catalytic reduction or electrolytically.

To improve solubility and to control the reaction temperature during the reactions, organic, inert solvents, such as lower alcohols and stable ketones and esters, alkyl halides, such as chloroform or 1,2-dichloroethane, ethers, such as dioxan, dimethoxyethane, diglyme, etc., may be used as co-solvents.

When all the ester groups $R^1$–$R^4$ in the tetraester according to the formula II are the same, the hydrolysis takes place stepwise according to the Scheme 1, and it is interrupted when the concentration of the desired partial ester is at its greatest.

In order to prepare a specific partial ester structure, it is advantageous to use a tetraester of the formula II wherein the ester groups are not the same (mixed tetraester), but contains groups which behave differently with respect to hydrolysis. It has, for example, been discovered that the hydrolysis rate of alkyl and silyl esters is dependant on the structure as follows:

$$\text{silyl} > \text{tert} > \text{sec} > \text{prim}$$

It is possible to fine tune the stepwise progress of the hydrolysis reaction also by means of the size and shape of the alkyl and silyl substituent as well as by electronical factors. In some instances advantage may be taken of a partial ester which is thermodynamically more favoured, for example, due to the formation of a chelate. It is often advantageous to perform a reesterification in order to change or improve the stepwise hydrolysis of the different ester sites. Especially the methylester may be converted to the corresponding acid over a silyl ester.

Pure partial esters may thus be prepared in an advantageous manner by performing a selective hydrolysis, if necessary stepwise, of a mixed tetraester of the formula II, which has been prepared using ester groups which are advantageous from the point of view of hydrolysis, or corresponding unhalogenated compounds, whereby the halogenation may be carried out after the hydrolysis.

Also selective hydrolysis reactions known especially from phosphate and monophosphonate chemistry may be used.

The progress of the hydrolysis may be followed for example chromatographically or by means of $^{31}$P-NMR and the reaction may be interrupted when the level of the desired partial ester is at its greatest and this may be isolated from the reaction mixture either as the free acid or as a salt by precipitation, extraction or chromatographically, and the salt form may be converted to the free acid or the free acid to its salt.

The compounds according to this invention may be prepared also by selective esterification of bisphosphonic acids in accordance with the above mentioned reaction Scheme 1 (the reaction takes place in the direction of the lower arrow).

As a starting material a (halogenmethylene) bisphosphonic acid according to the formula VII, or an unhalogenated bisphosphonic acid, which optionally is in the form of a salt, such as a metal or ammonium salt, or advantageously the corresponding phosphonic acid tetrachlorides are used, and depending on the desired end result, 1 to 4 equivalents of the desired aliphatic or aromatic-alcohol, or the corresponding activated alkylation, silylation and arylation reagents, such as orto-, imido- and vinylesters, ketene acetals and other suitable transfer reagents for alkyl-, silyl- and aryl groups, such as diazo compounds, active carboxylic acid esters, phosphates, phosphonates, phosphites, sulphates, and sulphonates. The reaction is preferably performed under anhydrous conditions, preferably in the temperature range of 0° to 150° C., or when using an inert co-solvent, at the boiling point thereof.

The esters II to IV may also be prepared in a nucleophilic substitution reaction between the bisphosphonate anion, often the ammonium salt of bisphosphonic acid, and an organic halide or sulphonate, or in a reaction of another reagent, such as of amidates, for example halogen acetamidate, further in a condensation reaction between a phosphonic acid group and alcohols or a phenols corresponding to the desired groups $R^1$–$R^4$, using a reagent for cleaving off water, such as carbodiimides and carbonyl- and sulphonylazoles, alkyl- or arylsulphonyl chlorides, such as TPS, or oxidative esterification, such as phosphine + azodicarboxylic ester. Pure partial esters, also mixed esters, may thus be prepared in an advantageous manner by selective esterification, if necessary stepwise, of halogenated bisphosphonic acids of the formula VII, or of corresponding unhalogenated, whereby the halogenation may be carried out after the esterification.

Also other selective esterification reactions may be used known primarily from phosphate and monophosphonate chemistry.

The progress of the esterification reactions may be followed, for example, chromatographically or using $^{31}$P-NMR and the reaction is interrupted when the content of the desired partial ester is at its greatest and this is isolated from the reaction mixture by precipitation, extraction or chromatographically and, if desired, a salt form obtained is converted to the free acid or the free acid is converted to its salt.

Partial esters of bisphosphonic acid according to the invention may also be prepared by constructing the P—C—P frame from its parts

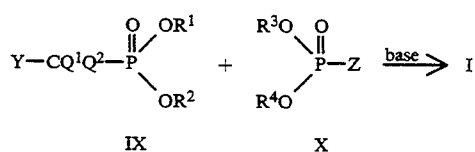

wherein in the formula Y is hydrogen or halogen or other leaving group, Z is halogen, aryloxy, sulphonyloxy or alkoxy, and $R^1$–$R^4$ and $Q^1$, $Q^2$ have the meaning given above, whereby $Q^2$ may also have the meaning of hydrogen. The base is for example NaH, BuLi, or LDA. When $Q^2$ is hydrogen, the halogenation is carried out after preparation of the frame. In the starting material optionally present free acid sites ($R^1$, $R^2$, $R^3$ or $R^4$=H) have to be neutralized, by using a sufficient amount of base, prior to the coupling reaction. The coupling reaction and the halogenation may be carried out in the same vessel as consecutive steps taking advantage of the already existing anionic site at the carbon.

Also the Michaelis-Arbuzov reactions may be used, whereby the compound of the formula X above is replaced by the corresponding phosphite, or the Michaelis-Becker reaction, whereby Z is hydrogen (cf. below).

The partial esters of bisphosphonic acids according to the invention may also be prepared from P—C—P—compounds at a lower oxidation level by oxidation (for example $P^{III} \rightarrow P^V$).

also have the meaning of fluorine. The halogenation takes place as will be described below. When one or more of the groups $R^1$ to $R^4$ is hydrogen, base has to be added in an amount sufficient to neutralize the free acid sites, as has been described above.

The partial esters of bisphosphonic acids according to the invention may be prepared also using stepwise the above mentioned processes known primarily from phosphate and monophosphonate chemistry.

Also other selective reactions known primarily from phosphate and monophosphonate chemistry may be used.

The partial esters I of bisphosphonic acid according to the invention may also be prepared from other partial esters VIII by performing an intra- or intermolecular

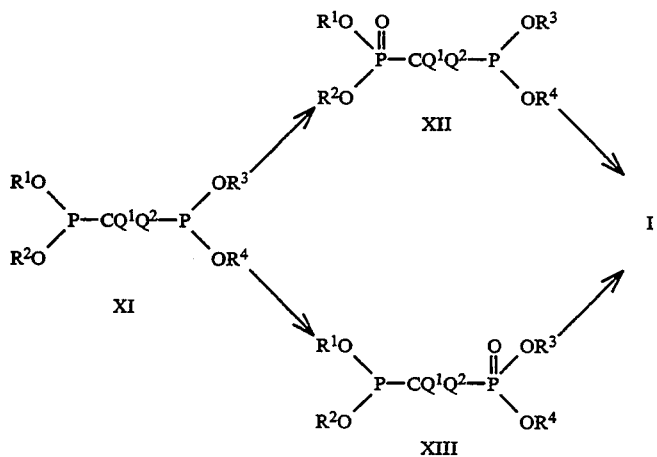

whereby in the formulas $R^1$-$R^4$ and $Q^1$, $Q^2$ have the meaning given above, whereby the phosphonite structure may exist in an equilibrium with the hydrogenphosphonate structure.

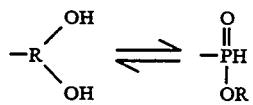

All conventional oxidation agents, or their solutions, such as hydrogen peroxide, perhalogen compounds, per acids, permanganate etc., may be used.

The partial esters of bisphosphonic acid according to the invention may also be prepared by halogenating the corresponding unhalogenated partial esters, also stepwise, or the halogen(s) may be replaced by others, or one out of two may be removed.

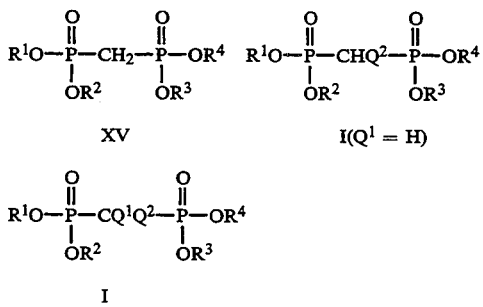

In the formulas $R^1$-$R^4$ and $Q^1$, $Q^2$ have the meaning given above, whereby in the exchange reactions $Q^2$ may exchange reaction

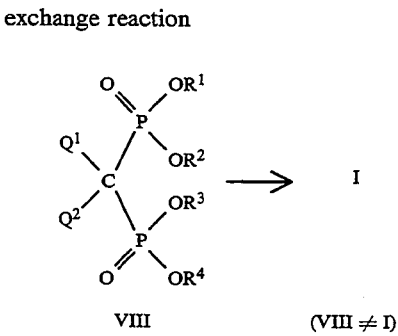

in which formula VIII $R^1$-$R^4$ and $Q^1$, $Q^2$ have the meaning given above.

Also the above mentioned reactions may be followed e.g. chromatographically or using $^{31}$P-NMR and interrupted when the content of the desired product is at its greatest, this product being isolated from the reaction mixture as the free acid or as its salt by precipitation, extraction or chromatographically, and if desired, the salt form is converted to the free acid or the free acid to its salt.

The tetraesters II and corresponding tetraacids IV used as starting materials in the above reactions may be prepared by processes known as such by constructing the P—C—P frame from its parts. Irrespective of the final partial ester, it is often advantageous to first prepare the tetraester according to the formula II using ester structures which are advantageous with respect to the preparation of the desired partial ester. In some cases, when preparing the biphosphonate frame, partial esters, especially symmetrical diester salts may be formed due to an immediate partial hydrolysis taking place under the reaction conditions.

The bisphosphonate frame may be prepared, for example, using the following known reactions:

a) The Michaelis-Becker reaction

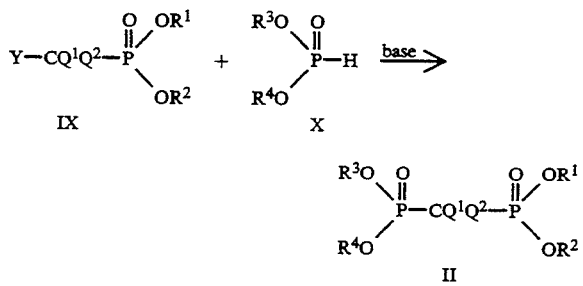

In the formulas $R^1$–$R^4$, and $Q^1$, $Q^2$ have the meaning given above, whereby also $Q^2$ may be hydrogen, and Y is halogen, acyloxy or sulphonyloxy. The base is Na, NaH, BuLi, LDA or KO-t-Bu/PTC.

b) The Michaelis-Arbuzov reaction

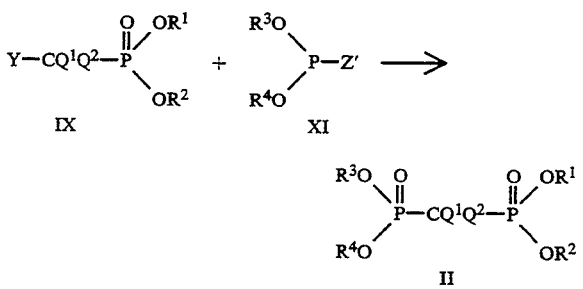

In the formulas $R^1$–$R^4$ and $Q^1$, $Q^2$ have the same meaning as above, whereby also $Q^2$ may be hydrogen, Y is halogen, acyloxy or sulphonyloxy, and Z' is alkoxy, silyloxy, acyloxy or sulphonyloxy.

c) The carbanion reaction

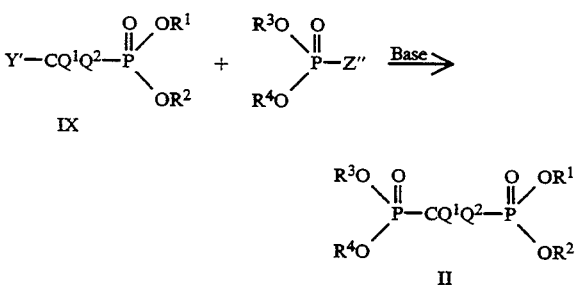

In the formulas $R^1$–$R^4$ and $Q^1$, $Q^2$ have the same meaning as in the formula II, whereby also $Q^2$ may be hydrogen, Y' is hydrogen or halogen, Z" is halogen, alkoxy, acyloxy or sulphonyloxy. The base is BuLi, LDA, AlkMgHal or Alk$_2$CuLi.

Taking into account the preparation of the desired partial ester the above prepared tetraesters II may, if necessary, be converted to other suitable tetraesters using exchange reactions. Thereby the groups OR$^1$–OR$^4$ may be exchanged directly or over the corresponding phosphonochloride (cf. above) or by applying other processes known primarily from phosphate and monophosphonate chemistry (cf. above).

Halogen atom(s) may be substituted for the hydrogens on the carbon between the phosphorous atoms in the bisphosphonate advantageously also in the form of the tetraester II, whereby the reaction advantageously is performed using a hypohalite. Also other conventional halogenation reactions may be used, such as the reactions of bisphosphono carbanions prepared using a strong base, with elemental halogens, or halogenation with N-haloamines and other active halides or polyhalogen compounds. It is, however, to be noted that contrary to what has been stated in the publication Zh. Obshch. Khim. 39 (1969) 845-8, the chlorination of the intermediate carbon with phosphorous pentachloride does not succeed (cf. e.g. J. Chem. Soc. (1966) 757, cf also Example 14). In the first mentioned publication is namely stated that the treatment of methylenebisphosphonic acid tetracyclohexyl ester with phosphorous pentachloride results in the symmetric (dichloromethylene)bisphosphonic acid dicyclohexyl ester. It seems, however, that this is a wrong conclusion based on an impure composition.

The halogen substituents of the carbon may also be introduced into the bisphosphonate structure as the halogenated monophosphonate IX, whereby $Q^1$ and/or $Q^2$ are halogens. The halogen on the carbon in the frame may also be substituted for hydrogen, usually by nucleophilic dehalogenation, or for a different halogen using known reactions. The mixed halogen compounds I may also be prepared by the stepwise use of the above mentioned halogenation or exchange reactions (cf. Phosphorus and sulfur, 37 (1988) 1).

Optically active partial esters I may be prepared best by using known optically active compounds, such as optically active alcohols, in the preparation of the above mentioned starting materials, intermediates and end products, or in the exchange reactions.

Bisphosphonates inhibit osteoclastic bone resorption. They are characterized by a non-hydrolyzable P—C—P bond which targets the compounds onto bone. They inhibit both formation and dissolution of the bone mineral (Fleisch, H. In: Peck WA, ed. Bone and Mineral Research, Amsterdam: Excerpta Medica, 1983:319 (Annual 1)). However, compounds which are good inhibitors of calcium phosphate crystallization, may cause as a side-effect an inhibition of mineralization.

In addition to their physicochemical interaction with calcium phosphate crystals, bisphosphonates also influence cellular metabolism (Shinoda H. et al., Calcif Tissue Int 1983; 35:87). The exact mechanism of inhibition of bone resorption has not yet been clarified. Moreover, the effects seem to vary from one bisphosphonate to another.

Bisphosphonates are absorbed, stored and excreted unaltered. The intestinal absorption is usually below 5% of the oral dose. A remarkable part of the absorbed bisphosphonate is localised in bone, the reminder being rapidly excreted in the urine. The half-life of circulating bisphosphonates is short, the rate of entry into bone being fast. On the other hand, the half-life of the skeletal retention is long.

One aim of the present invention is to introduce new bisphosphonate derivatives which have lower affinity for bone to avoid side-effects without loosing activity for bone resorption inhibition. Simultaneously increasing their absorption after oral administration could lead into better therapeutic agents for the treatment of bone diseases.

The biological activity of compounds according to the invention for preventing bone resorption in vitro and in vivo has been measured, as well as the interaction of the compounds with bone mineral and their relative bioavailability after oral dosing. It was found that they exhibited lower affinity for bone than the reference compound clodronate. Despite this they have restored their biological activity as indicated by in vitro and in vivo resorption assay. In addition, the compounds are better absorbed after oral administration than clodronate.

The partial esters of mono- or dihalogenated methylenebisphosphonic acids may thus be used as pharmaceuticals as such, or as their pharmacologically acceptable salts, such as the alkali or ammonium salts. Such salts may be prepared by reacting the ester acids with the corresponding inorganic or organic bases. Depending on the reaction conditions, the ester salts are formed directly in the above mentioned reactions under the reaction conditions used for preparing the compounds of the formula I.

The new compounds I according to this invention may be administered enterally or parenterally. All conventional administration forms, such as tablets, capsules, granules, syrups, solutions and suspensions may be used. Also all adjuvants for manufacture, solubility and administration of the preparation, as well as stabilizers, viscosity regulating and dispersion agents and buffers may be used.

Such adjuvants include inter alia tartrate and citrate buffers, alcohols, EDTA and other nontoxic complexing agents, solid and liquid polymers and other sterile substrates, starch, lactose, mannite, methylcellulose, talc, silicic acids, fatty acids, gelatine, agar-agar, calcium phosphate, magnesium stearate, animal and vegetable fats and, if desired, flavouring and sweetening agents.

The dosage depends on several factors, for example on the manner of administration, species, age and individual condition. The daily doses are about 1 to 1000 mg, usually 10 to 200 mg per person, and they may be administered as a single dose or may be divided into several doses.

In the following, examples of a typical capsule and a tablet are given:

|  | mg/caps. |
|---|---|
| Capsule | |
| Active ingr. | 100.0 mg |
| Starch | 20.0 mg |
| Magn. stear. | 1.0 mg |
| Tablet | |
| Active ingr. | 400.0 mg |
| Microcryst. cell. | 20.0 mg |
| Lactose | 67.0 mg |
| Starch | 10.0 mg |
| Talc | 4.0 mg |
| Magn. stear. | 1.0 mg |

For medicinal use also a parenterally administered preparation may be made, for example an infusion concentrate or injection. In the infusion concentrate e.g. sterile water, phosphate buffer, NaCl, NaOH or HCl or other suitable known pharmaceutical adjuvants may be used, in the injections also suitable pharmaceutical preservatives.

It is also possible to formulate a topical formulation administered in a suitable vehicle.

The compounds in ester-acid form are liquid or waxy substances, usually soluble in organic solvents and in some instances in water. The ester salts are solid, crystalline or typically powdery substances which usually dissolve well in water, in some instances in organic solvents, and only a few structures being poorly soluble in all solvents. The compounds are very stable, also in their neutral solutions at room temperature.

The structure of the compounds may easily be verified with $^1$H-, $^{13}$C- and $^{31}$P-NMR-spectroscopy and FAB-masspectrometry or when silylated with EI-masspectrometry. For concentration and impurity determinations $^{31}$P-NMR-spectroscopy is very suitable. For polar compounds as such ion exchange and exclusion-HPLC may be used and for tetraesters and silylated ester acid derivatives GLC or GC/MS may be used. From the compounds sodium and other metals were determined separately as well as the possible crystal water content. From the amine salts, nitrogen was determined.

The following examples illustrate the invention without limiting the same.

EXAMPLE 1:

Trihexyl (dichloromethylene)bisphosphonate and monosodium salt 29.1 g (0.05 moles) of tetrahexyl (dichloromethylene)bisphosphonate ($^{31}$P-NMR (CDCl$_3$): δ 8.85) and 290 ml of pyridine are refluxed for about 1 hour (the reaction is followed with $^{31}$P-NMR) and the mixture is evaporated under a vacuum. The residue (trihexyl (dichloromethylene)bisphosphonate N-hexyl pyridinium salt) is dissolved in 300 ml of toluene and the solution is washed with 2×100 ml of 1 N NaOH and 100 ml of water and dried (MgSO4) and filtered. The filtrate is evaporated under a vacuum. The waxy evaporation residue is dissolved in 100 ml of CH$_3$OH and the solution is treated with activated carbon and filtered. The filtrate is evaporated to constant weight under a vacuum, whereby about 21 g (80% of the theor.) of (dichloromethylene)bisphosphonic acid trihexyl ester monosodium salt are obtained ($^{31}$P-NMR (D$_2$): δ 13.06 (P), 5.18 (P'), $^2J_{PP}$=18.0 Hz), at a concentration of 95% and wherefrom trihexyl (dichloromethylene)bisphosphonate may be liberated with acid treatment.

I.a. the following methylenebisphosphonic acid triesters and corresponding sodium salts may be prepared in an analogous manner:

From tetrabutyl (dichloromethylene)bisphosphonate: tributyl (dichloromethylene)bisphosphonate from tetrapentyl (dichloromethylene)bisphosphonate: tripentyl (dichloromethylene)bisphosphonate from tetraheptyl (dichloromethylene)bisphosphonate: triheptyl (dichloromethylene)bisphosphonate from tetrapropyl (dichloromethylene)bisphosphonate: tripropyl (dichloromethylene)bisphosphonate from tetraisopropyl (dichloromethylene)bisphosphonate: triisopropyl (dichloromethylene)bisphosphonate (monosodium salt) ($^{31}$P-NMR(D$_2$O): δ 11.87 (P), 5.19 (P') $J_{PP}$=17.3 Hz)

from tetraethyl (dichloromethylene)bisphosphonate: (triethyl (dichloromethylene)bisphosphonate N-ethylpyridinium salt isolated as an intermediate ($^{31}$P-NMR (D$_2$O): δ 12 47 (P), 1.30 (P'), $^2J_{PP}$=17.5 Hz triethyl (dichloromethylene)bisphosphonate (monosodium salt) (31P-NMR (D$_2$O): δ 13.47 (P), 5.58 (P') $^2J_{PP}$=17.0 Hz)

from tetrakis(1-methylbutyl) (dichloromethylene)bisphosphonate: tris(1-methylbutyl) (dichloromethylene)bisphosphonate from tetrakis(1-ethylpropyl) (dichloromethylene)bisphosphonate: tris(1-ethylpropyl) (dichloromethylene)bisphosphonate from tetracyclopentyl (dichloromethylene)bisphosphonate: tricyclopentyl (dichloromethylene)bisphosphonate from tetraallyl (dichloromethylene)bisphosphonate: triallyl (dichloromethylene)bisphosphonate from tetraphenyl (dichloromethylene)bisphosphonate: triphenyl (dichloromethylene)bisphosphonate from tetrabenzyl (dichloromethylene)bisphosphonate: tribenzyl (dichloromethylene)bisphosphonate from tetramethyl (dichloromethylene)bisphosphonate: trimethyl (dichloromethylene)bisphosphonate ($^{31}$P-NMR (CDCl$_3$): δ 16.46 (P), 3.42 (P'), $^2J_{PP}$=19.6 Hz), (monosodium salt)($^{31}$P-NMR (CDCl$_3$): δ 15.74 (P), 6.58 (P'), $^2J_{PP}$=17.0 Hz) (tributylammonium salt)($^{31}$P-NMR (CDCl$_3$): δ 15.50 (P), 4.25 (P'), 16.6 Hz)

from tetra-(Z)-3-hexenyl (dichloromethylene)bisphosphonate: tri-(Z)-3-hexenyl (dichloromethylene)bisphosphonate (N-(Z)-3-hexenyl pyridinium salt) ($^{31}$P-NMR (CDCl$_3$): δ 12.53 (P), 4.70 (P') $^2J_{PP}$=17.5 Hz) from P,P-diethyl P',P'-diisopropyl (dichloromethylene)bisphosphonate: P,P-diisopropyl P'-ethyl (dichloromethylene)bisphosphonate (N-ethyl pyridinium salt) ($^{31}$P-NMR (CDCl$_3$): δ 11.81 (P) 5.95 (P') $^2J_{PP}$=16.6 Hz) from P,P-diisopropyl P',P'-dimethyl (dichloromethylene)bisphosphonate: P,P-diisopropyl P'-methyl (dichloromethylene)- bisphosphonate (tributylmethyl ammonium salt) ($^{31}$P-NMR (CDCl$_3$): δ 11.12 (P), 4.85 (P'), 17.3 Hz)

from P,P-diisopropyl P',P'-dihexyl (dichloromethylene)bisphosphonate: P,P-diisopropyl P'-hexyl (dichloromethylene)bisphosphonate (N-hexyl pyridinium salt) ($^{31}$P-NMR (CDCl$_3$): δ 8.67 (P) 6.57 (P'), $^2J_{PP}$=20.9 Hz)

from tetra(3-chlorophenyl) (dichloromethylene)bisphosphonate: tri(3-chlorophenyl) (dichloromethylene)bisphosphonate from tetra(3-phenyl 2-propenyl) (dichloromethylene)bisphosphonate: tri(3-phenyl 2-propenyl) (dichloromethylene)bisphosphonate from tetra(2-butunyl) (dichloromethylene)bisphosphonate: tri(2-butynyl) (dichloromethylene) bisphosphonate from tetrahexyl (dibromomethylene)bisphosphonate: trihexyl (dibromomethylene)bisphosphonate from tetraisopropyl (dibromomethylene)bisphosphonate: triisopropyl (dibromomethylene)bisphosphonate from tetracyclopentyl (dibromomethylene)bisphosphonate: tricyclopentyl (dibromomethylene)bisphosphonate from tetraethyl (monobromomethylene)bisphosphonate: triethyl (monobromomethylene)bisphosphonate from tetrahexyl (monobromomethylene)bisphosphonate: trihexyl (monobromomethylene)bisphosphonate from tetraisopropyl (monobromomethylene)bisphosphonate: triisopropyl (monobromomethylene)bisphosphonate from tetracyclopentyl (monobromomethylene)bisphosphonate: tricyclopentyl (monobromomethylene)bisphosphonate from tetraisopropyl (diiodomethylene)bisphosphonate: triisopropyl (diiodomethylene)bisphosphonate from tetraphenyl (diiodomethylene)bisphosphonate: triphenyl (diiodomethylene)bisphosphonate from tetraisopropyl (monoiodomethylene)bisphosphonate: triisopropyl (monoiodomethylene)bisphosphonate from tetraisopropyl (monochloromethylene)bisphosphonate: triisopropyl (monochloromethylene)bisphosphonate from tetracyclopentyl (monochloromethylene)bisphosphonate: tricyclopentyl (monochloromethylene)bisphosphonate.

from tetraethyl (monochloromethylene)bisphosphonate: triethyl (monochloromethylene)bisphosphonate from tetrahexyl (monochloromethylene)bisphosphonate: trihexyl (monochloromethylene)bisphosphonate from tetracyclohexyl (monochloromethylene)bisphosphonate: tricyclohexyl (monochloromethylene)bisphosphonate Tetrahexyl (dichloromethylene)bisphosphonate used as a starting material above may be prepared in the following manner:

17.6 g (0.1 moles) of methylenebisphosphonic acid and 253 g (0.8 moles) of trihexyl ortoformate are refluxed for 3 h and then distilled under a vacuum until the inner temperature is about 170° C.1 mmHg. As the distillation residue, about 51 g (100% of theor. ) of tetrahexyl methylenebisphosphonate ($^{31}$P-NMR (CDCl$_3$) : δ 20.04) are obtained as a colourless oil, the concentration of which is 90%.

25.6 g (0.05 moles) of tetrahexyl methylenebisphosphonate are added while stirring to 250 ml of a 10 NaOCl-solution at 0° C. during about 30 minutes, whereafter stirring is continued for 1 h at 0° C. and 2 h at room temperature. The mixture is extracted with 2×100 ml of toluene and the combined extracts are washed with 50 ml of 1N NaOH and 2×50 ml of water and dried (MgSO$_4$) and filtered. The filtrate is evaporated under a vacuum whereby about 25 g (85% of the theor.) of tetrahexyl (dichloromethylene)bisphosphonate are obtained ($^{31}$P-NMR (CDCl$_3$): δ 8.85), having a concentration of 95%.

I.a. the following (dichloromethylene)bisphosphonic acid tetraesters may be prepared in an analogous manner:

From tetrabutyl methylenebisphosphonate ($^{31}$P-NMR (CDCl$_3$): δ 20.30): tetrabutyl (dichloromethylene)bisphosphonate ($^{31}$P-NMR (CDCl$_3$): δ 8.86)

from tetrapentyl methylenebisphosphonate ($^{31}$P-NMR (CDCl$_3$): δ 20.06): tetrapentyl (dichloromethylene)bisphosphonate ($^{31}$P-NMR (CDCl$_3$): δ 6 8.85)

from tetraheptyl-methylenebisphosphonate ($^{31}$P-NMR (CDCl$_3$): δ 20.07): tetraheptyl (dichloromethylene)bisphosphonate ($^{31}$P-NMR (CDCl$_3$): δ 8.86)

from tetrapropyl methylenebisphosphonate: tetrapropyl (dichloromethylene)bisphosphonate from tetraisopropyl methylenebisphosphonate ($^{31}$P-NMR (CDCl$_3$): δ 17.92): tetraisopropyl (dichloromethylene)bisphosphonate ($^{31}$P-NMR (CDCl$_3$): δ 7.21)

from tetramethyl methylenebisphosphonate ($^{31}$P-NMR (CDCl$_3$): δ 23.27): tetramethyl (dichloromethylene)bisphosphonate ($^{31}$P-NMR (CDCl$_3$): δ 10.88)

from tetraethyl methylenebisphosphonate ($^{31}$P-NMR (CDCl$_3$): δ 19.92): tetraethyl (dichloromethylene)bisphosphonate ($^{31}$P-NMR (CDCl$_3$): δ 8.82)

from tetrakis(1-methylbutyl) methylenebisphosphonate ($^{31}$P-NMR (CDCl$_3$): δ 6 18.10 (m)): tetrakis(1-methylbutyl) (dichloromethylene)bisphosphonate ($^{31}$P-NMR (CDCl$_3$): δ 7.69)

from tetrakis(1-ethylpropyl) methylenebisphosphonate ($^{31}$P-NMR (CDCl$_3$): δ 18.37): tetrakis(1-ethylpropyl) (dichloromethylene)bisphosphonate ($^{31}$P-NMR (CDCl$_3$): δ 7.89)

from tetracyclopentyl methylenebisphosphonate ($^{31}$P-NMR (CDCl$_3$): δ 18.74): tetracyclopentyl (dichloromethylene)bisphosphonate ($^{31}$P-NMR (CDCl$_3$): δ 7.51)

from tetraallyl methylenebisphosphonate ($^{31}$P-NMR (CDCl$_3$): δ 20.60): tetraallyl (dichloromethylene)bisphosphonate ($^{31}$P-NMR (CDCl$_3$): δ 9.21)

from tetra=(Z)-3-hexenyl methylenebisphosphonate ($^{31}$P-NMR (CDCl$_3$): δ 20.12): tetra-(Z)-3-hexenyl (dichloromethylene)bisphosphonate ($^{31}$P-NMR (CDCl$_3$): δ 8.72 (m))

from tetrakis(2-methyl-2-propenyl) methylenebisphosphonate ($^{31}$P-NMR (CDCl$_3$) : δ 20.31): tetrakis(2-methyl-2-propenyl) (dichloromethylene)bisphosphonate ($^{31}$P-NMR (CDCl$_3$): δ 9.06)

from tetraphenyl methylenebisphosphonate: tetraphenyl (dichloromethylene)bisphosphonate from tetrabenzyl methylenebisphosphonate ($^{31}$P-NMR (CDCl$_3$): 20.66): tetrabenzyl (dichloromethylene)bisphosphonate.

Tetrahexyl (dibromomethylene)bisphophonate useful as a starting material may be prepared in the following manner.

Into a sodium hypobromite solution, which has been prepared by introducing 8.4 g of bromine into 4.6 g of NaOH in 50 ml of water, are added dropwise while stirring 10.2 g (0.02 moles) of tetrahexyl methylenebisphosphonate during appr. 10 minutes at 0° to 5° C. The mixture is stirred for one hour while cooling and one hour at room temperature and is extracted with methylene chloride. The extract is washed with water and dried (MgSO$_4$) and filtered. The filtrate is evaporated under vacuum, whereby appr. 10.5 g (80% of the theor.) of tetrahexyl (dibromomethylene)bisphosphonate are obtained ($^{31}$P-NMR (CDCl$_3$): δ 6 8.98 ppm) as a colourless oil, at a concentration of 97%.

I.a. the following (dibromomethylene)bisphosphonic acid tetraesters may be prepared in an analogous manner:

Tetramethyl (dibromomethylene)bisphosphonate
tetraethyl (dibromomethylene)bisphosphonate
tetraisopropyl (dibromomethylene)bisphosphonate
tetracyclopentyl (dibromomethylene)bisphosphonate ($^{31}$P-NMR (CDCl$_3$): δ 7.26)
tetrabutyl (dibromomethylene)bisphosphonate
tetrapentyl (dibromomethylene)bisphosphonate Tetrahexyl (monobromomethylene)bisphosphonate useful as a starting material may be prepared in the following manner:

Into a solution containing 6.7 g (0.01 moles) of tetrahexyl (dibromomethylene)bisphosphonate in 70 ml of abs. ethanol, 2.5 g of SnCl$_2$ ×2H$_2$O in 100 ml of water are added while stirring at 0° C. After the addition, the mixture is stirred for 15 minutes and extracted with chloroform and the extract is dried (MgSO$_4$) and filtered. The filtrate is evaporated under a vacuum, whereby about 4.1 g (70% of the theor.) of tetrahexyl (monobromomethylene)bisphosponate ($^{31}$P-NMR (CDCl$_3$): δ 13.83 ppm) are obtained as a colourless oil, at a concentration of 90%.

I.a. the following (monobromomethylene)bisphosphonic acid tetraesters may be prepared in an analogous manner:

Tetramethyl (monobromomethylene)bisphosphonate
tetraethyl (monobromomethylene)bisphosphonate
tetraisopropyl (monobromomethylene)bisphosphonate
tetracyclopentyl (monobromomethylene)bisphosphonate Tetraisopropyl (monoiodomethylene)bisphosphonate useful as a starting material may be prepared in the following manner:

To 17.2 g (0.05 moles) of tetraisopropyl methylenebisphosphonate in 300 ml of a 10% K$_2$CO$_3$-solution, is added dropwise while stirring during about 20 minutes a solution, which contains 6.35 g of I$_2$ and 20 g of KI in 50 ml of water. After the addition the mixture is stirred for 2 h and the solution is extracted with ×150 ml of CH$_2$Cl$_2$. The extracts are combined and washed with a saturated NaCl-solution and dried (MgSO$_4$) and filtered. The filtrate is evaporated under a vacuum, whereby a evaporation residue of about 20 g is obtained as an almost colourless oil. According to $^{31}$P-NMR, the product contains 44% of tetraisopropyl (monoiodomethylene)bisphosphonate ($^{31}$P-NMR (CDCl$_3$:δ 14.17) and 56% of the starting material.

Tetraisopropyl (monochloromethylene)bisphosphonate useful as a starting material may be prepared in the following manner.

Into a solution containing 8.2 g (0.02 moles) of tetraisopropyl (dichloromethylene)bisphosphonate in 70 ml of ethanol, 9.0 g of sodium sulphite in 250 ml of water are added while stirring during 15 minutes at 10° to 15° C., whereafter the mixture is stirred for 1 h. The mixture is extracted with chloroform and the extract is dried (MgSO$_4$) and filtered. The filtrate is evaporated under a vacuum, whereby about 7.6 g (100% of the theor.) of tetraisopropyl (monochloromethylene)bisphosphonate ($^{31}$P-NMR (CDCl$_3$: δ 12.04 ppm) are obtained as a colourless oil, at a concentration of 98%.

I.a. the following (monochloromethylene)bisphosphonic acid tetraesters may be prepared in an analogous manner.

Tetramethyl (monochloromethylene)bisphosphonate
tetraethyl (monochloromethylene)bisphosphonate
tetracyclopentyl (monochloromethylene)bisphosphonate
tetracyclohexyl (monochloromethylene)bisphosphonate.

Example 2:

P,P'-Dihexyl (dichloromethylene)bisphosphonate bis(N-hexylpyridinium) and disodium salt 29.1 g (0.05 moles) of tetrahexyl (dichloromethylene)bisphosphonate and 290 ml of pyridine are refluxed for 1 day and the mixture is evaporated under a vacuum, whereby (dichloromethylene)bisphosphonic acid P,P'-dihexyl ester bis(N-hexylpyridinium) salt is obtained. This is dissolved in 180 ml of toluene and to the solution is added—while stirring effectively—125 ml of 2N NaOH. The gelatinous precipitate is separated by filtration and is washed with acetone and ethyl acetate and dried in a vacuum desiccator whereby about 11.5 g (50% of the theor.) of (dichloromethylene)bisphosphonic acid P,P'-dihexylester disodium salt ($^{31}$P-NMR (D$_2$): δ 8.97) are obtained, at a concentration of 96%- The P,P'-dihexyl (dichloromethylene)bisphosphonate may be liberated from its salt by treatment with an acid. In place of pyridine also other amines may be used, such as heterocyclic amines (morpholine, see Ex. 7), piperidine, piperazine, etc.) or aliphatic, primary, secondary or tertiary amines (di-isopropyl amine, triethyl amine, aniline, etc.).

I.a. the following symmetrical (dichloromethylene)-bisphosphonic acid diesters and their diamine and disodium salts may be prepared in an analogous manner:

From tetramethyl (dichloromethylene)bisphosphonate: P,P'-dimethyl (dichloromethylene)bisphosphonate (disodium salt) ($^{31}$P-NMR (D$_2$O): δ 10.00) (dipiperidinium salt) ($^{31}$P-NMR (D$_2$O ): δ 9.70)

from tetraethyl (dichloromethylene)bisphosphonate: P,P'-diethyl (dichloromethylene)bisphosphonate ($^{31}$P-NMR (D$_2$O): δ 9.22) (disodium salt), 8.86 (dipiperidinium salt), 7.04 (bis(N-ethyl pyridinium) salt)

from tetrapropyl (dichloromethylene)bisphosphonate: P,P'-dipropyl(dichloromethylene)bisphosphonate from tetraisopropyl (dichloromethylene)bisphosphonate: P,P'-diisopropyl (dichloromethylene)bisphosphonate ($^{31}$P-NMR(D$_2$O): δ 7.93 (acid) 8.26 (disodium salt), 7.83 (diammonium salt), 8.23 (dilitium salt))

from tetrabutyl (dichloromethylene)bisphosphonate: P,P'-dibutyl (dichloromethylene)bisphosphonate from tetrapentyl (dichloromethylene)bisphosphonate: P,P'-dipentyl (dichloromethylene)bisphosphonate from tetraheptyl (dichloromethylene)bisphosphonate: P,P'-diheptyl (dichloromethylene)bisphosphonate from tetracyclopentyl (dichloromethylene)bisphosphonate: P,P'-dicyclopentyl (dichloromethylene)bisphosphonate from tetraallyl (dichloromethylene)bisphosphonate: P,P'-diallyl (dichloromethylene)bisphosphonate from tetrakis(2-methyl-2-propenyl) (dichloromethylene)bisphosphonate: P,P'-bis(2-methyl-2-propenyl) (dichloromethylene)bisphosphonate ($^{31}$P-NMR (D$_2$O: δ 8.60 (dipiperidinium salt)

from tetracyclohexyl (dichloromethylene)bisphosphonate: P,P'-dicyclohexyl (dichloromethylene)bisphosphonate from tetraphenyl (dichloromethylene)bisphosphonate: P,P'-diphenyl (dichloromethylene)bisphosphonate from tetrabenzyl (dichloromethylene)bisphosphonate: P,P'-dibenzyl (dichloromethylene)bisphosphonate from P,P'-dimethyl P,P'-diethyl (dichloromethylene) bisphosphonate P-methyl P'-ethyl (dichloromethylene)bisphosphonate ($^{31}$P-NMR (CDCl$_3$): δ 10.03 (P), 8.74 (P'), $^2$J$_{PP}$=15.5 Hz (bis(N-methyl piperazinium salt)).

Example 3:

P,P-Dihexyl (dichloromethylene)bisphosphonate and its disodium salt 5.0 g (0.01 moles) of P,P-dihexyl P',P'-di-isopropyl (dichloromethylene)bisphosphonate is dissolved in 100 ml of toluene and to the solution 6.7 g (0.07 moles) of methane sulphonic acid are added and the solution is stirred while heating and the progress of hydrolysis is followed with $^{31}$P-NMR. When the reaction has reached a suitable stage, the mixture is cooled to room temperature and the lower phase is separated. The toluene phase is washed with 10 ml of water and dried (MgSO$_4$) and evaporated to constant weight under a vacuum, whereby appr. 3.3 g (80% of the theor.) of P,P-dihexyl (dichloromethylene)bisphosphonate ($^{31}$P-NMR (CDCl$_3$): δ 11.89 ppm, (P') 5.27 ppm, $^2$J$_{PP}$, 21.0 Hz), are obtained, at a concentration of 95%.

2.07 g (0.005 moles) of the above bisphosphonic acid is mixed with 25 ml of water and the pH of the mixture is adjusted to 9-10 with 1.0 N NaOH. The mixture is evaporated to dryness under a vacuum and the evaporation is repeated after the addition of isopropanol. The residue is mixed with acetone-isopropanol (1:1) and the precipitate is filtered and dried. The yield is about 1.8 g (80% of the theor.) of (dichloromethylene)bisphosphonic acid P,P-dihexylester disodium salt, at a concentration of 97%.

I.a. the following unsymmetrical (dichloromethylene)-bisphosphonic acid diesters and corresponding sodium salts may be prepared in an analogous manner:

from P,P-dibutyl P',P'-diisopropyl (dichloromethylene)-bisphosphonate ($^{31}$P-NMR (CDCl$_3$): δ 9.02 (P), 7.17 (P') $^2$J$_{PP}$=23.0 Hz)): P,P-dibutyl (dichloromethylene)bisphosphonate from P,P-dipentyl P',P'-diisopropyl (dichloromethylene)bisphosphonate: P,P-dipentyl (dichloromethylene)bisphosphonate from P,P-diheptyl P',P'-diisopropyl (dichloromethylene)bisphosphonate: P,P-diheptyl (dichloromethylene)bisphosphonate from P,P-diethyl P',P'-ditert-butyl (dichloromethylene)bisphosphonate: P,P-diethyl (dichloromethylene)bisphosphonate from P,P-di-4-methylphenyl P',P'-ditert-butyl (dichloromethylene)bisphosphonate: P,P-di-4-methylphenyl (dichloromethylene)bisphosphonate from P-decyl P-propyl P',P'-ditert-butyl (dichloromethylene)bisphosphonate: P-decyl P-propyl (dichloromethylene)bisphosphonate.

By using an aqueous solution of the acid the following compounds may be prepared in an analogous manner:

from P,P-diethyl P',P'-isopropyl (dichloromethylene)-bisphosphonate: P,P-diethyl P'-isopropyl (dichloromethylene)bisphosphonate ($^{31}$P-NMR (CDCl$_3$): δ 13 86 (P), 5 12 (P') $^2$J$_{PP}$=17.0 Hz)

from P,P-diisopropyl P',P'-dihexyl (dichloromethylene)bisphosphonate: P,P-dihexyl P'-isopropyl (dichloromethylene) bisphosphonate ($^{31}$P-NMR (CDCl$_3$) : δ 10.41 (P), 5.71 (P'), $^2$J$_{PP}$=21.0 Hz) .

P,P-Dihexyl P',P'-diisopropyl (dichloromethylene)-bisphosphonate used as a starting material above may be prepared in the following manner:

To a THF-hexane solution of LDA (litium diisopropyl amide) which contains appr. 0.072 moles of LDA, are added while stirring (N$_2$-atmosphere) at −78° C. 9.0 g (0.034 moles) of dihexylmethyl phosphonate in 10 ml of anhydrous TMF, whereafter stirring is continued for 15 minutes. To the mixture are added while stirring at −78° C. 7.2 g (0.036 moles) of diisopropyl chlorophosphate in 10 ml of anhydrous TMF, whereafter stirring is continued for 15 minutes at −78° C. and the mixture is allowed to warm to −50° C. To the mixture is added 5 N HCl to a pH of 5 to 6, whereafter the mixture is evaporated under a vacuum. The residue is extracted with 3×50 ml of CHCl$_3$ and the combined extracts are washed with a 10% NaHCO$_3$ solution and water and is dried (MgSO$_4$) and evaporated. The residue is stirred into ether and filtered. The filtrate is evaporated to dryness under a vacuum, whereby about 13 g (90% of the theor.) of P,P-dihexyl P',P'diisopropyl methylenebisphosphonate ($^{31}$P-NMR (CDCl$_3$): δ 20.13 (P), 17.84 (P'), $^2$J$_{PP}$=7.6 Hz) are obtained, at a concentration of 90%. The same product is obtained with a yield of about 80% in the above manner but substituting the dihexyl methyl phosphonate with 8.5 g (0.034 moles) of dihexyl hydrogen phosphonate and the diisopropyl chlorophosphate with 7.7 g (0.036 moles) of diisopropyl (chloromethyl) phosphonate.

To a mixture containing 32.8 g of NaHCO$_3$ in 130 ml of a 5% NaOCl solution, are added while stirring vigorously at 0° C. 10.7 g (0.025 moles) of P,P-dihexyl P',P'-diisopropyl methylenebisphosphonate during 15 minutes. After the addition the mixture is stirred for 2 h at 0° C. and 2 h at room temperature and extracted with 2×100 ml of toluene. The combined extracts are washed with 2×75 ml of water and dried (MgSO$_4$) and filtered. The filtrate is evaporated under a vacuum, whereby appr. 10 g (80% of the theor.) of P,P-dihexyl P',P'-diisopropyl (dichloromethylene)bisphosphonate ($^{31}$P-NMR (CDCl$_3$): δ 8 98 (P'), 4.72 (P'), $^2J_{PP}$=22 9 Hz) are obtained as a colourless oil at a concentration of 90%.

An alternative method for the preparation of an unsymmetrical starting tetraester, P,P-diethyl P',P'-diisopropyl methylenebisphosphonate, is presented in the following.

Step 1:

To 134 g (0.5 moles) of methylene iodide are added while stirring at 160° C. (N$_2$-atmosphere) 66 g (0.31 moles) of triisopropyl phosphite during 30 minutes, simultaneously distilling off liberated isopropyl iodide. After the addition stirring is continued for 40 min at 160° to 165° C. and the mixture is fractionated under vacuum. The yield is appr. 62 g (65% of the theor.) of diisopropyl (iodomethyl)phosphonate, b.p. 100° to 103° C./4 mm ($^{31}$P-NMR (CDCl$_3$): δ 18.54), at a concentration of 95%.

Step 2:

To 30.6 g (0.1 moles) of diisopropyl (iodomethyl)-phosphonate are added gradually while stirring at 185° to 205° C. (N$_2$-atmosphere) 83 g (0.5 moles) triethyl phosphite while the liberated ethyl iodide is distilled off. After the addition stirring is continued for 10 min at 210° C. and the mixture is cooled and fractionated under a vacuum. The yield is appr. 12.5 g (40% of the theor.) of P,P-diethyl P',P'-diisopropyl methylenebisphosphonate, b.p. 140–150 °C/2 mm ($^{31}$P-NMR (CDCl$_3$) : δ 17.77 (P) 20 20 (P') $^2J_{PP}$=7.4 Hz), at a concentration of 95%. I.a. the following unsymmetrical (dichloromethylene)-bisphosphonic acid P,P,P',P'-tetraesters may be prepared in an analogous manner:

from P,P-dimethyl P',P'-diethyl methylenebisphosphonate ($^{31}$P-NMR (CDCl$_3$): δ 22.65 (P) 19.55 (P'), $^2J_{PP}$=6.00 Hz) P,P-dimethyl P',P'-diethyl (dichloromethylene)bisphosphonate ($^{31}$P-NMR (CDCl$_3$): δ 11.17 (P) 8.45 (P') $^2J_{PP}$=23.1 Hz)

from P,P-dimethyl P',P'-diisopropyl methylenebisphosphonate ($^{31}$P-NMR (CDCl$_3$): δ 23.00 (P) 17.43 (P') $^2J_{PP}$=7.1 Hz): P,P-dimethyl P',P'-diisopropyl (dichloromethylene)bisphosphonate ($^{31}$P-NMR (CDCl$_3$): δ 11.56 (P), 6.79 (P') $^2J_{PP}$=22.8 Hz)

from P,P-Diethyl P',P'-diisopropyl methylenebisphosphonate ($^{31}$P-NMR (CDCl$_3$): δ 20.20 (P) 17.77 (P') $^2J_{PP}$=7.4 Hz): P,P-Diethyl P',P'-diisopropyl (dichloromethylene)bisphosphonate ($^{31}$P-NMR (CDCl$_3$): δ 9.16 (P) 7.16 (P') $^2J_{PP}$=22.8 Hz)

from P,P-diethyl P',P'-di-tert-butyl methylenebisphosphonate ($^{31}$P-NMR (CDCl$_3$): δ 20.88 (P) 10.68 (P') $^2J_{PP}$=13.3 Hz): P,P-diethyl P',P'-di-tert-butyl (dichloromethylene)bisphosphonate ($^{31}$P-NMR (CDCl$_3$): δ 10.38 (P) −0.37 (P') $^2J_{PP}$=19.0 Hz)

from P,P-diphenyl P',P'-dibenzyl methylenebisphosphonate ($^{31}$P-NMR (CDCl$_3$): δ 12.77 (P) 19.27 (P'), $^2J_{PP}$=9.0 Hz): P,P-diphenyl P',P'-dibenzyl (dichloromethylene)bisphosphonate ($^{31}$P-NMR (CDCl$_3$): δ 0.43 (P) 8.87 (P') $^2J_{PP}$=22.9 Hz)

from P,P-dibutyl P',P'-diisopropyl methylenebisphosphonate ($^{31}$P-NMR (CDCl$_3$): δ 20.22 (P') 17.90 (P') $^2J_{PP}$=7.9 Hz): P,P-dibutyl P',P'-diisopropyl (dichloromethylene)bisphosphonate ($^{31}$P-NMR (CDCl$_3$): δ 9.02 (P) 7.17 (P') $^2J_{PP}$=23.0 Hz)

from P,P-dipentyl P',P'-diisopropyl methylenebisphosphonate P,P-dipentyl P',P'-diisopropyl (dichloromethylene)bisphosphonate from P,P-diheptyl P',P'-diisopropyl methylenebisphosphonate: P,P-diheptyl P',P'-diisopropyl (dichloromethylene)bisphosphonate from P,P,P'-trimethyl P'-isopropyl methylenebisphosphonate ($^{31}$P-NMR (CDCl$_3$): δ 22.82 (P) 17.64 (P'), $^2J_{PP}$=6.3 Hz): P,P,P'-trimethyl P'-isopropyl (dichloromethylene)bisphosphonate ($^{31}$P-NMR (CDCl$_3$): δ 11.24 (P), 8.91 (P'), 23.1 Hz)

from P,P,P'-trimethyl P'-hexyl methylenebisphosphonate: P,P,P'-trimethyl P'-hexyl (dichloromethylene)-bisphosphonate from P,P,P'-trimethyl P'-octadecyl methylenebisphosphonate: P,P,P'-trimethyl P'-octadecyl (dichloromethylene)bisphosphonate from P,P-diisopropyl P'-octadecyl P'-tert-butyl methylenebisphosphonate ($^{31}$P-NMR (CDCl$_3$): δ 15.76 (P), 18.35 (P'), $^2J_{PP}$=9.2 Hz): P,P-diisopropyl P'-octadecyl P'-tert-butyl (dichloromethylene)bisphosphonate from P,P-dimethyl P',P'-diphenyl methylenebisphosphonate ($^{31}$P-NMR (CDCl$_3$): δ 20.95 (P) 12.84 (P') $^2J_{PP}$7.9 Hz): P,P-dimethyl P',P'-diphenyl (dichloromethylene)bisphosphonate ($^{31}$P-NMR (CDCl$_3$): δ 10.37 (P) 0.17 (P') $^2_{PP}$=23.2 Hz)

EXAMPLE 4:

Monohexyl (dichloromethylene) bisphosphonate and its trisodium salt 4.7 g (0.01 moles) of P-hexyl P-tert-butyl P',P'-diisopropyl (dichloromethylene)bisphosphonate (prepared by chlorinating according to the Example 1 P-hexyl P-tert-butyl P',P'-diisopropyl methylenebisphosphonate prepared from hexyl tert-butyl chlorophosphate and diisopropyl methylphosphonate in accordance with the Example 3) are stirred with 30 ml of 2N hydrochloric acid for 1 to 2 h at about 80° C. (the progress of hydrolysis is followed with $^{31}$P-NMR). After the reaction the mixture is evaporated to constant weight under a vacuum, whereby monohexyl (dichloromethylene)bisphosphonate is obtained as an oily residue. The evaporation residue is dissolved in water and 5.0 ml of a 2 N NaOH solution are added and evaporated to constant weight under a vacuum. The solid residue is washed with ethanol and dried to constant weight. The yield is about 3.5 g (90% of the theor.) of (dichloromethylene)bisphosphonic acid monohexyl ester trisodium salt ($^{31}$P-NMR (D$_2$O): δ 11.50 (P), 9.36 (P'), $^2J_{PP}$=15.7 Hz), at a concentration of 98%.

The group to be removed may in place of the tert-butyl, isopropyl etc group also be a methyl group, which then may be hydrolysed selectively for example over the silyl ester (cf. Example 10).

I.a. the following (dichloromethylene)bisphosphonic acid monoesters and corresponding sodium salts may be prepared in an analogous manner (also the corresponding tetraesters used as starting materials have been prepared in an analogous manner, cf. Examples 1 and 3):

from P-propyl P-tert-butyl P',P'-diisopropyl (dichloromethylene)bisphosphonate: monopropyl (dichloromethylene)bisphosphonate from P-butyl P-tert-butyl P',P'-diisopropyl (dichloromethylene)bisphosphonate monobutyl (dichloromethylene)bisphosphonate from P-pentyl p-tert-butyl P',P'-diisopropyl (dichloromethylene)bisphosphonate: monopentyl(dichloromethylene)bisphosphonate from P-heptyl p-tert-butyl P',P'-diisopropyl ( dichloromethylene)bisphosphonate: monoheptyl (dichloromethylene)bisphosphonate from P-decyl P-tert-butyl P',P'-diisopropyl (dichloromethylene)bisphosphonate: monodecyl (dichloromethylene)bisphosphonate from P-dodecyl p-tert-butyl P',P'-diisopropyl (dichloromethylene)bisphosphonate: monododecyl (dichloromethylene)bisphosphonate from P-octadecyl p-tert-butyl P',P'-diisopropyl (dichloromethylene)bisphosphonate: mono-octadecyl (dichloromethylene)bisphosphonate from P-allyl P-tert-butyl P',P'-diisopropyl (dichloromethylene)bisphosphonate: monoallyl (dichloromethylene)bisphosphonate from P-phenyl P-tert-butyl P',P'-diisopropyl (dichloromethylene)bisphosphonate: monophenyl (dichloromethylene)bisphosphonate from P-benzyl P-tert-butyl P',P'-diisopropyl (dichloromethylene)bisphosphonate: monobenzyl (dichloromethylene)bisphosphonate from P-cyclohexyl P-tert-butyl P',P'-diisopropyl (dichloromethylene)bisphosphonate: monocyclohexyl (dichloromethylene)bisphosphonate from P-phenyl-P-tert-butyl P',P'-diisopropyl (monochloromethylene)bisphosphonate:
monophenyl (monochloromethylene)bisphosphonate from P-4-bromo-phenyl P-tert-butyl P',P'-diisopropyl (dichloromethylene)bisphosphonate: 4-bromo-phenyl (dichloromethylene)bisphosphonate.

EXAMPLE 5:

Tri-isopropyl (dichloromethylene)bisphosphonate and monosodium salt 413 g (1 mole) of tetraisopropyl (dichloromethylene)-bisphosphonate are mixed with 4.1 l of water and the mixture is stirred under reflux for 1.5 h and is evaporated to a volume of appr. 750 ml. The solution is made alkaline while cooling with a 50% NaOH solution and is left to stand at room temperature for appr. 3 days and is filtered. The filtrate is diluted with 315 ml of methanol and stirred for 16 h at room temperature. The mixture is filtered and the filtrate is evaporated to appr. 140 ml and left to stand for 5 days at room temperature. The precipitate is filtered and washed with 3×25 ml of methanol and dried to constant weight at 50° C. The yield is appr. 44 g (11%) of (dichloromethylene)bisphosphonic acid triisopropylester monosodium salt ($^{31}$P-NMR (CDCl$_3$): δ 11.87 (P) 5.19 (P') $^2J_{PP}$=17.3 Hz FAB-MS: m/z 393/395/397 (M+H)), at a concentration of 90% and which by treatment with an acid may be converted to triisopropyl (dichloromethylene)bisphosphonate.

EXAMPLE 6:

P,P'-Diisopropyl (dichloromethylene)bisphosphonate, mono- and disodium salt (step 1). Monoisopropyl (dichloromethylene)bisphosphonate and tri-sodium salt (step 2)

Step 1:

413 g (1 mole) of tetraisopropyl (dichloromethylene)-bisphosphonate are mixed with 4.1 l of water and the mixture is stirred under reflux for 4 h and evaporated to a volume of appr. 870 ml. The solution is made alkaline while cooling with a 30% NaOH solution and left to stand at room temperature for appr. 3 days and filtered (the filtrate is collected —see step 2). The precipitate is stirred for 2 h with 190 ml of a 5 N NaOH solution and the mixture is filtered. The precipitate is washed with 30 ml of ethanol and is thereafter stirred in 190 ml of abs. ethanol. The mixture is filtered and the precipitate is washed with 70 ml of abs. ethanol and dried to constant weight at 100° C. The yield is appr. 115 g ($^{31}$% of the theor.) of (dichloromethylene) bisphosphonic acid P,P'-diisopropylester disodium salt ($^{31}$P-NMR (D$_2$O): δ 8.26) FAB-MS: m/z 373/375/377 (M+H)), at a concentration of 99.5% and which with acid treatment may be converted to P,P'-diisopropyl (dichloromethylene)bisphosphonate from which the corresponding monosodium salt may be prepared by adding 1 equivalent of NaOH to the aqueous solution of the acid.

Step 2:

The filtrate obtained in the first filtration in the previous step is evaporated to a volume of appr. 410 ml and is left to stand at room temperature for appr. 16 h. The precipitate is filtered off and the pH of the filtrate is adjusted a 8.5 with concentrated hydrochloric acid and a solution is added containing 95 ml of methanol and 63 ml of water and the mixture is stirred for 3 days at room temperature. The mixture is filtered and the precipitate washed with 30 ml of methanol and dried to constant weight at 100 ° C. The yield is appr. 38 g (11% of the theor.) of (dichloromethylene) bisphosphonic acid monoisopropyl ester trisodium salt ($^{31}$P-NMR (D$_2$O ): δ 10.95 (P), 9.54 (P'), $^2J_{PP}$=16.6 Hz FAB-MS: m/z 353/355/357 (M+H)) at a concentration of 97% and which with acid treatment may be converted to monoisopropyl (dichloromethylene)bisphosphonate.

EXAMPLE 7:

P,P'-diisopropyl (dichloromethylene)bisphosphonate and dimorpholinium salt 12.4 g (0.03 moles) of tetraisopropyl (dichloromethylene) bisphosphonate, 120 ml of morpholine and 60 ml of chloroform are stirred under reflux for 3 h and left to stand at appr. 4° C. for 1 day. The mixture is filtered and the precipitate is washed with 60 ml of chloroform and dried. The yield is appr. 12.5 g (83% of the theor.) (dichloromethylene) bisphosphonic acid diisopropyl ester dimorpholinium salt ($^{31}$P-NMR (D$_2$O): δ 7.86), at a concentration of 94% and from which P,P'-diisopropyl (dichloromethylene)bisphosphonate may be liberated with acid treatment. When instead of morpholine other secondary amines are used, such as piperidine, dibutyl amine etc., the corresponding diamine salt, e.g. dipiperidinium and dibutylammonium salt of (dichloromethylene)bisphosphonic acid P,P'-diisopropyl ester is obtained (cf. Example 2). The reaction may also be carried out in the absence of a co-solvent.

I.a. the following symmetrical (dichloromethylene) bisphosphonic acid diester dimorpholinium salts may be prepared in an analogous manner:

From tetraethyl (dichloromethylene)bisphosphonate: P,P'-diethyl (dichloromethylene)bisphosphonate ($^{31}$P-NMR (D$_2$O): δ 8.88)

from tetraisopropyl (dichloromethylene)bisphosphonate: P,P-diisopropyl (dichloromethylene)bisphosphonate ($^{31}$P-NMR (D$_2$O): δ 7.86)

from tetracyclopentyl (dichloromethylene)bisphosphonate: P,P'-dicyclopentyl (dichloromethylene)bisphosphonate ($^{31}$P-NMR (D$_2$O): δ 8.38) from tetrakis(1-methylbutyl) (dichloromethylene)bisphosphonate: P,P'-Bis(1-methylbutyl) (dichloromethylene)bisphosphonate ($^{31}$P-NMR (D$_2$O): δ 8.24)

from tetrakis(1-ethylpropyl) (dichloromethylene)bisphosphonate: P,P'-bis(1-ethylpropyl) (dichloromethylene)bisphosphonate from P,P-diisopropyl P',P'-dimethyl (dichloromethylene)bisphosphonate: p-isopropyl P'-methyl (dichloromethylene)bisphosphonate from tetra-(Z)-3-hexenyl (dichloromethylene) bisphosphonate P,P'-di-(Z)-3-hexenyl (dichloromethylene)bisphosphonate from P,P-diphenyl P',P'-dibenzyl (dichloromethylene) bisphosphonate P-phenyl P'-benzyl (dichloromethylene)phosphonate from P,P-diisopropyl P',P'-diethyl (dichloromethylene)bisphosphonate: P-isopropyl P'-ethyl (dichloromethylene)bisphosphonate from P,P-diisopropyl P',P'-dibutyl (dichloromethylene)bisphosphonate: P-isopropyl P'-butyl (dichloromethylene)bisphosphonate from P,P-diisopropyl P',P'-dihexyl (dichloromethylene)bisphosphonate: P-isopropyl P'-hexyl (dichloromethylene)bisphosphonate ($^{31}$P-NMR (CDCl$_3$): δ 6.87 (P) 7.67 (P'), $^2$J$_{PP}$=20.4 Hz)

from P,P,P'-triethyl P'-bicyclo[2.2.1]heptan-2-yl (dichloromethylene)bisphosphonate: P-bicyclo[2.2.1]heptan-2-yl P'-ethyl (dichloromethylene)bisphosphonate from P,P,P'-triethyl P'-propargyl (dichloromethylene)bisphosphonate: P-propargyl P'-ethyl (dichloromethylene)bisphosphonate from P,P,P'-triethyl P'-4-methoxyphenyl (dichloromethylene)bisphosphonate: P-4-methoxyphenyl P'-ethyl (dichloromethylene)bisphosphonate from P,P-diethyl P',P'-dimethyl (monochloromethylene)bisphosphonate: P-ethyl P'-methyl (monochloromethylene)bisphosphonate (dipiperidinium salt) ($^{31}$P-NMR (D$_2$O): δ 12.05 (P), 13.05 (P'), 2.7 Hz)

from tetraallyl (monochloromethylene)bisphosphonate: P,P'-diallyl (monochloromethylene)bisphosphonate from tetraallyl (dibromomethylene)bisphosphonate: P,P'-diallyl (dibromomethylene)bisphosphonate from tetrahexyl (dibromomethylene)bisphosphonate: P,P'-dihexyl (dibromomethylene)bisphosphonate ($^{31}$P-NMR (D$_2$O): δ 11.92)

from tetrahexyl (monobromomethylene)bisphosphonate P,P'-dihexyl (monobromomethylene)bisphosphonate ($^{31}$P-NMR (D$_2$O): δ 8.44)

from tetracyclopentyl (monobromomethylene)bisphosphonate: P,P'-dicyclopentyl (monobromomethylene)bisphosphonate (dipiperidinium salt) ($^{31}$P-NMR (D$_2$O): δ 8.47)

from tetraethyl (dibromomethylene)bisphosphonate: P,P'-diethyl (dibromomethylene)bisphosphonate from tetrabutyl (dibromomethylene)bisphosphonate: P,P'-dibutyl (dibromomethylene)bisphosphonate from tetrapentyl (dibromomethylene)bisphosphonate: P,P'-dipentyl (dibromomethylene)bisphosphonate from tetracyclopentyl (dibromomethylene)bisphosphonate: ($^{31}$P-NMR (D$_2$O): δ 7.26) P,P'-dicyclopentyl (dibromomethylene)bisphosphonate.

The used (halogenmethylene)bisphosphonic acid (mixed) tetra esters have been prepared according to the methods disclosed in the Examples 1 and 3.

EXAMPLE 8:

Tetramethyl (dichloromethylene)bisphosphonate and trimethyl (dichloromethylene)bisphosphonate 1.2 g (0.05 moles ) of anhydrous finely divided (dichloromethylene)bisphosphonic acid are stirred in 100 ml of anhydrous chloroform and into the mixture are added dropwise while stirring at 15° to 20° C. 53 ml of a 2% ether solution of diazomethane. After the addition stirring is continued for 30 min at room temperature and the mixture is evaporated to constant weight under a vacuum. The yield is appr. 1.5 g (100% of the theor.) of tetramethyl (dichloromethylene)bisphosphonate ($^{31}$P-NMR (CDCl$_3$): δ 10.88), at a concentration of 98%.

When mixing tetramethyl (dichloromethylene)bisphosphonate in aqueous ether for-3 h under reflux, pure trimethyl (dichloromethylene)bisphosphonate is obtained with a yield of over 90% ($^{31}$P-NMR (CDCl$_3$): δ 16.46 (P) 3.42 (P') $^2$J$_{PP}$=19.6 Hz).

EXAMPLE 9:

Monohexyl (dichloromethylene)bisphosphonate and trisodium salt 3.19 g (0,01 moles) of (dichloromethylene)bisphosphonyl tetrachloride (distilled, b.p. 105° to 110° C./1 mm) are dissolved in 30 ml of anhydrous toluene and to the solution are added dropwise while stirring at 0° to 5° C. 1.02 g (0.01 moles) of 1-hexanol in 10 ml of anhydrous toluene. After the addition stirring is continued for 30 min at 0° to 5° C. and 1 h at appr. 25° C. and 10 ml of water is added dropwise and the mixture is stirred vigorously for 1 h at 30 to 40 ° C. The solution is cooled to room temperature and the pH is adjusted to 10 to 11 with 2 N NaOH and evaporated to constant weight under a vacuum. The residue contains about 60% of (dichloromethylene)bisphosphonic acid monohexyl ester trisodium salt which can be purified by fractional crystallisation from water-methanol. The yield is appr. 1.8 g (45% of the theor.) and concentration >90%. ($^{31}$P-NMR (D$_2$O): δ 11 50 (P), 9 36 (P'), $^2$J$_{PP}$=15.7 Hz).

EXAMPLE 10:

P,P-diisopropyl (dichloromethylene)bisphosphonate and disodium salt 7.4 g (0.02 moles) of P,P-diisopropyl-P',P'-dimethyl (dichloromethylene)bisphosphonate are dissolved in 75 ml of anhydrous acetonitrile and 6,0 g of sodium iodide are added as well as 22.4 g of chlorotrimethyl silane. The mixture is stirred for 15 min under reflux and evaporated under a vacuum, whereby P,P-diisopropyl P',P'-bis(trimethylsilyl) (dichloromethylene)bisphosphonate ($^{31}$P-NMR (CDCl$_3$): δ 7.50 (P), −9.61, (P'), $^2$J$_{PP}$=24.3 Hz) is obtained. This is hydrolyzed by adding 25 ml of water of a temperature of appr. 50° C., whereafter the solution is made alkaline with a 10% NaOH solution and is evaporated to constant weight under a vacuum.

The solid residue is mixed in 50 ml of acetone and is left standing in ice water for 4 h. The precipitate is filtered and washed with acetone and dried to constant weight at 70° C. The yield is appr. 6.8 g (88% of the theor.) of (dichloromethylene)bisphosphonic acid P,P-diisopropyl ester disodium salt ($^{31}$P-NMR (D$_2$O): δ 14.52 (P), 7.20 (P'), $^2$J$_{PP}$=16.0 Hz) at a concentration of 98% and which with acid treatment may be converted to the corresponding acid.

I.a. the following (dichloromethylene)bisphosphonic acid silyl and partial esters may be prepared by analogous methods:

from P,P-dimethyl P',P'-diethyl (dichloromethylene)-bisphosphonate: P,P-bis(trimethylsilyl) P',P'-diethyl (dichloromethylene)bisphosphonate, wherefrom P',P'-diethyl (dichloromethylene)bisphosphonate ($^{31}$P-NMR (CDCl$_3$): δ 16.67 (P), 7.20 (P') $^2$J$_{PP}$=15.5 (sodium salt))

from P,P,P'-trimethyl P'-hexyl (dichloromethylene)bisphosphonate: P,P,P'-tris(trimethylsilyl) P'-hexyl (dichloromethylene) bisphosphonate, wherefrom monohexyl (dichloromethylene)bisphosphonate ($^{31}$P-NMR (D$_2$O): δ 11.50 (P), 9.36 (P'), $^2$J$_{PP}$=15.74 Hz (trisodium salt))

from P,P,P'-triisopropyl P'-methyl (dichloromethylene)bisphosphonate: P,P,P'-triisopropyl P'-trimethylsilyl (dichloromethylene) bisphosphonate, wherefrom P,P,P'-triisopropyl (dichloromethylene)bisphosphonate ($^{31}$P-NMR (CDCl$_3$): δ 11.87 (P) 5.19 (P'), $^2$J$_{PP}$=17.2 Hz (monosodium salt))

from P,P,P'-trimethyl P-isopropyl (dichloromethylene)bisphosphonate: P,P,P'-tris(trimethylsilyl) P-isopropyl (dichloromethylene bisphosphonate ($^{31}$P-NMR (CDCl$_3$): δ −1.18 (P), −9.71 (P') $^2$J$_{PP}$=27.1 Hz) wherefrom, monoisopropyl (dichloromethylene)bisphosphonate from P,P-diisopropyl P',P'-dimethyl (dichloromethylene)bisphosphonate: P,P-diisopropyl P'-methyl P'-trimethylsilyl (dichloromethylene)bisphosphonate ($^{31}$P-NMR (CDCl$_3$): δ 7.81 (P), 1.12 (P'), $^2$J$_{PP}$=23.3 Hz), wherefrom P,P-diisopropyl P'-methyl (dichloromethylene)bisphosphonate, from P,P,P'-trimethyl P'-octadecyl (dichloromethylene)bisphosphonate: P,P,P'-tris(trimethylsilyl) P'-octadecyl (dichloromethylene)bisphosphonate, wherefrom octadecyl (dichloromethylene)bisphosphonate and trisodium salt from P,P-dimethyl P',P'-diphenyl (dichloromethylene)-bisphosphonate: P,P-bis(trimethylsilyl) P',P'-diphenyl (dichloromethylene) bisphosphonate ($^{31}$P-NMR (CDCl$_3$): δ −11.26 (P), 2.03 (P') $^2$J$_{PP}$=26. 6 Hz) wherefrom P,P-diphenyl (dichloromethylene)bisphosphonate ($^{31}$P-NMR (D$_2$O): δ 6.48 (P) 11.01 (P') $^2$J$_{PP}$=14.7 Hz (disodium salt))

from P,P,P'-trimethyl P'-(3-methyl-2-cyclohexenyl) (dichloromethylene)bisphosphonate P,P,P'-tris(-trimethylsilyl) P'-(3-methyl-2-cyclohexenyl) (dichloromethylene)bisphosphonate, wherefrom (3-methyl-2-cyclohexenyl) (dichloromethylene) bisphosphonate ($^{31}$P-NMR (D$_2$O): δ 9.25, 8.81 $^2$J$_{PP}$=17,6 Hz (trisodium salt))

from P,P'-diphenyl P,P'-dimethyl (dichloromethylene)-bisphosphonate: P,P'-bis(trimethylsilyl) P,P'-triphenyl (dichloromethylene)bisphosphonate, wherefrom P,P'-diphenyl (dichloromethylene)bisphosphonate from P,P,P'-trimethyl P'-farnesyl (dichloromethylene)-bisphosphonate: P,P,P'-tris(trimethylsilyl) P'-farnesyl (dichloromethylene)bisphosphonate, wherefrom monofarnesyl (dichloromethylene)bisphosphonate from P,P,P-trimethyl P'-1-tetrahydronaphtyl (dichloromethylene)bisphosphonate: P,P,P'-tris(trimethylsilyl) P'-1-tetrahydronaphtyl (dichloromethylene)bisphosphonate, wherefrom 1-tetrahydronaphtyl (dichloromethylene)bisphosphonate from P,P-diethyl P',P'-dimethyl (monochloromethylene)bisphosphonate: P,P-diethyl P',P'-bis(trimethylsilyl) (monochloromethylene)bisphosphonate, wherefrom P,P-diethyl (monochloromethylene)bisphosphonate from P,P,P'-trimethyl P'-1-octadecyl (dibromomethylene)bisphosphonate: P,P,P'-tris(-trimethylsilyl) P'-1-octadecyl (dibromomethylene)-bisphosphonate, wherefrom 1-octadecyl (dibromomethylene)bisphosphonate:

an analogous manner the following compounds may be prepared:

from P,P-diethyl P',P'-dimethyl (dichloromethylene)-bisphosphonate: P,P-diethyl P',P'-bis(t-butyldimethylsilyl) (dichloromethylene)bisphosphonate, wherefrom P,P-diethyl P'-t-butyldimethylsilyl) (dichloromethylene)bisphosphonate ($^{31}$P-NMR (CDCl$_3$): δ 9.70 (P), −1.06 (P'), $^2$J=23.7 Hz)

tetraethyl (dichloromethylene)bisphosphonate: P,P'-diethyl p,p,-bis(t-butyldimethylsilyl) (dichloromethylene)bisphosphonate, wherefrom P,P'-diethyl P-t-butyldimethylsilyl (dichloromethylene) bisphosphonate ($^{31}$P-NMR (CDCl$_3$): δ 7.05 (P), 0.68 (P'), $^2$J$_{PP}$23.4 Hz) from tetramethyl (dichloromethylene)bisphosphonate: P-methyl P,P',P'-tris(t-butyldiphenylsilyl)-(dichloromethylene)bisphosphonate ($^{31}$P-NMR (CDCl$_3$): δ 1.18–12.08 (P,P'), 35.9 Hz)

EXAMPLE 11:

P,P'-di-isopropyl (dichloromethylene)bisphosphonic acid monobarium, monocalcium, mono- and dipotassium, mono- and dilitium and mono, and diammonium salts 3.29 g (0.01 moles) of P,P'-diisopropyl (dichloromethylene)bisphosphonic acid are dissolved in 22 ml of water and while stirring 3.15 g (0.01 moles) of Ba(OH)$_2$×8H$_2$O are added and stirring is continued for 2 h. The mixture is filtered and the filtrate is evaporated to constant weight under a vacuum. The yield is appr. 4.5 g (96% of the theor.) of colourless crystalline P,P'-diisopropyl (dichloromethylene)bisphosphonic acid monobarium salt at a concentration of >98%.

In an analogous manner i.a. the monocalcium salt, the mono- and dipotassium salt, the mono- and dilitium salt as well as the mono- and diammonium salt (yield >95%, concentration >98%) have been prepared.

EXAMPLE 12:

P,P'-diisopropyl (monochloromethylene)bisphosponate and dimorpholinium salt 8.2 g (0.02 moles) of tetraisopropyl (dichloromethylene)bisphosphonate (prepared as has been described in the Example 1) in 80 ml of morpholine are stirred under reflux for 24 h and the solution is cooled. The formed precipitate is separated and recrystallized from ether. The yield is appr. 8.5 g (90% of the theor.) of colourless crystalline P,P'-diisopropyl (monochloromethylene)bisphosphonate ($^{31}$P-NMR (D$_2$O): δ 11.31 ppm (dimorpholinium salt)) at a concentration of appr. 85% (the product contains appr. 15% of the corresponding dichloro compound) and wherefrom the corresponding acid may be liberated by treating an aqueous solution of the product with two equivalents of hydrochloric acid. I.a. the following (monochloromethylene)bisphosphonic acid diesters have been prepared in an analogous manner:

P,P'-Diethyl (monochloromethylene)bisphosphonate ($^{31}$P-NMR (D$_2$O): δ 12.40 ppm (dipiperidium salt))
P,P'-Dicyclopentyl (monochloromethylene)bisphosphonate ($^{31}$P-NMR (D$_2$O): δ 6 11.87 ppm (dipiperidinium salt). Example 13:

Monoethyl (dichloromethylene)bisphosphonate and trisodium salt 5.0 g (0.014 moles) of tetraethyl (dichloromethylene)bisphosphonate and 6.7 g (0.045 moles) of NaI are dissolved in 50 ml of anhydrous CH3CN and while stirring 12.2 g (0.112 moles) of trimethylsilyl chloride are added. After the addition stirring is continued at room temperature, protected from moisture, for appr. 4 days and is evaporated under a vacuum. To the mixture obtained as a residue (contains as the major component monoethyl tris(trimethylsilyl) (dichloromethylene)bisphosphonate) 10 ml of water are added and the mixture is made alkaline with a 10% NaOH solution. The mixture is diluted with 50 ml of CH$_3$OH and is left standing at +4° C. for 2 h and is filtered (the precipitate is (dichloromethylene)bisphosphonic acid sodium salt). To the filtrate 25 ml of ethanol are added and it is left standing for 1 day at +4° C. and is filtered. The filtrate is evaporated under a vacuum and the residue is washed with acetone and filtered. The precipitate is dried to constant weight whereby appr. 2.0 g (50% of the theor.) of colourless crystalline (dichloromethylene)bisphosphonic acid monoethyl ester trisodium salt are obtained ($^{31}$P-NMR (D$_2$O): δ 6 11.86 (P), 9.40 (P') $^2$J$_{PP}$=15.4 Hz) at a concentration of >90% and wherefrom the corresponding acid may be liberated with acid treatment.

In an analogous manner monomethyl (dichloromethylene)bisphosphonate and its trisodium salt ($^{31}$P-NMR (D$_2$O): δ 10.58 (P) 8.58 (P') $^2$J=16.7 Hz) has been prepared from tetramethyl (dichloromethylene)bisphosphonate; (disodiummonopiperidinium salt) $^{31}$P-NMR (D$_2$0O): δ 12.97 (P), 9.17 (P'), 15.1Hz).

EXAMPLE 14:

Treatment of tetraispropyl (methylene)bisphosphonate with phosphorous pentachloride 3.44 g (0.01 moles) of tetraisopropyl (methylene)bisphosphonate were treated, while stirring, in portions with 4.16 g (0.02 moles) of PCl$_5$, whereby the mixture warmed to appr. 50° C. After the addition stirring was continued for 2 h and the clear solution was evaporated under a vacuum.

To the residue were added while cooling 20 ml of water and after the termination of the exothermic reaction the mixture was stirred under reflux for 30 min and evaporated under a vacuum. The clear oil obtained as a residue was analysed using $^{31}$p- and $^1$H-NMR and the composition was found to be the following:

| | δ $^{31}$P-NMR (NaOD) | mole % |
|---|---|---|
| Methylenebisphosphonate | 17.17 | 21.5 |
| Monoisopropyl methylene bisphosphonate | 19.94, 14.74, $^2$J$_{PP}$ = 8.2 Hz | 41 |
| P,P'-diisopropylmethylene-bisphosphonate | 17.24 | 20 |
| Phosphate | 3.33 | 15 |

-continued

| | δ $^{31}$P-NMR (NaOD) | mole % |
|---|---|---|
| Monoisopropylphosphate | 3.62 | 2.5 |

There were no signs that the hydrogens on the intermediate carbon had been exchanged to chlorine atoms.

EXAMPLE 15:

Tetracyclopentyl (bromochloromethylene)bisphosphonate and P,P'-dicyclopentyl (bromochloromethylene) bisphosphonate and its dipiperidinium salt 4.8 g (0.01 moles) of tetracyclopentyl (monochloromethylene)bisphosphonate ($^{31}$P-NMR (CDCl$_3$): δ 12.44 ppm, $^2$J$_{PH}$=17.7 Hz) are dissolved in 20 ml of carbontetrachloride and 0.55 g of bensyltriethylammonium chloride and 20 ml of a 10% sodium hypobromite solution are added while cooling and stirring at about 10° C. The mixture is stirred vigorously for 30 min at about 10° C. and the organic phase is separated, washed with water, dried (Na$_2$SO$_4$) and filtered. The filtrate is evaporated in a vacuum, whereby about 5.0 g (90% of the theor.) of tetracyclopentyl (bromochloromethylene)bisphosphonate ($^{31}$P-NMR (CDCl$_3$): δ 7.68 ppm) is obtained as a colourless oil at a concentration of >80%.

2.8 g (0.005 moles) of the above obtained tetracyclopentyl (bromochloromethylene)bisphosphonate are dissolved in 6 ml of anhydrous piperidine and the mixture is stirred for 1 h on an oil bath of about 110° C. and evaporated in a vacuum.

The solid residue is mixed with 10 ml of ether and the precipitate filtered and dried. The yield is about 1.8 g (60% of the theor.) of colourless crystalline P,P'-dicyclohexyl (bromochloromethylene)bisphosponate, diperidinium salt ($^{31}$P-NMR (D$_2$O): δ 8.47 ppm), at a concentration of >90% and wherefrom the corresponding acid may be liberated by treating with an acid.

EXAMPLE 16

Trimethyl (monobromomethylene)bisphosphonate and its litium salt 1.04 g (2.5 moles) of the tributyl methyl ammonium salt of trimethyl methylenebisphosphonate (prepared as described in the Example 1 from tetramethyl methylenebisphosphonate and tributyl amine ($^{31}$P-NMR (CDCl$_3$): 30.51 ppm (P), 9.54 ppm (P'), $^2$J$_{PP}$=6.9 Hz)) are dissolved in 40 ml of anhydrous THF and the mixture is cooled to −70° C and while stirring 4.0 ml (5.0 moles) of a 2.5 M hexane solution of BuLi is added at about −70° C. and stirring is continued for a further 10 minutes. To the mixture is added while stirring at about −60° C. 0.80 g (5.0 mmoles) of bromine in 20 ml of anhydrous THF within 10 minutes, whereafter stirring is continued for 15 minutes at about −60° C. and the mixture is heated to room temperature. The mixture is filtered and the filtrate is evaporated in a vacuum, whereby about 0.6 g (80% of theor.) of trimethyl (monobromomethylene)bisphosphonate, litium salt is obtained ($^{31}$P-NMR (CDCl$_3$): δ 25.03 ppm (P), 11.59 (P'), $^2$J$_{PP}$=15.4 Hz), which by treatment with an acid may be converted to the corresponding acid.

We claim:

1. A compound comprising a bisphosphonic acid derivative of the formula I

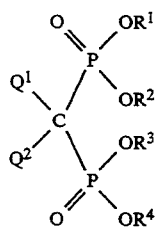

including the stereoisomers optically active isomers thereof, and including a pharmaceutically acceptable salt thereof, wherein $R^1$, $R^2$, $R^3$ and $R^4$ are independently selected from the group consisting of $C_1$–$C_7$-alkyl, and hydrogen, at least one of the groups $R^1$, $R^2$, $R^3$ and $R^4$ is hydrogen, at least one of the groups $R^1$, $R^2$, $R^3$ and $R^4$ is different from hydrogen, $Q^1$ is selected from the group consisting of hydrogen and chlorine, and $Q^2$ is chlorine.

2. The compound of claim 1, wherein $Q^1$ and $Q^2$ are chlorine.

3. The compound of claim 2, wherein one of the groups $R^1$–$R^4$ is hydrogen, one of the groups $R^1$–$R^4$ is lower alkyl and the others are selected from the group consisting of hydrogen and lower alkyl.

4. The compound of claim 3, where the compound is selected from the group consisting of monomethyl (dichloromethylene)bisphosphonic acid and monoethylester (dichloromethylene)bisphosphonic acid.

5. The compound of claim 3, wherein two of the groups $R^1$–$R^4$ are lower alkyl.

6. A pharmaceutical composition wherein the pharmaceutically active agent comprises a compound of the general formula I according to the claim 1.

* * * * *

UNITED STATES PATENT AND TRADEMARK OFFICE
CERTIFICATE OF CORRECTION

PATENT NO. : 5,376,649

DATED : December 27, 1994

INVENTOR(S) : Pohjala et al.

Page 1 of 4

It is certified that error appears in the above-indentified patent and that said Letters Patent is hereby corrected as shown below:

At col. 4, line 10, delete "v" and substitute therefore -- V --

At col. 6, line 66, delete "Nail" and substitute therefore -- NaH --

At col. 12, line 43, delete "$^{31}P$-NMR ($D_2$)" and substitute therefore -- $^{31}P$-NMR ($D_2O$) --

At col. 12, line 65, delete "12 47" and substitute therefore -- 12.47 --

At col. 12, line 65, after "Hz" insert -- ) --

At col. 14, line 25, delete "°C.1" and substitute therefore -- °C/1 --

At col. 14, line 31, after "10" insert -- % --

At col. 14, line 50, delete "6"

At col. 15, line 39, delete "6"

UNITED STATES PATENT AND TRADEMARK OFFICE
CERTIFICATE OF CORRECTION

PATENT NO. : 5,376,649
DATED : December 27, 1994
INVENTOR(S) : Pohjala et al.

It is certified that error appears in the above-indentified patent and that said Letters Patent is hereby corrected as shown below:

At col. 16, line 63, delete "$(D_2)$" and substitute therefore -- $(D_2O)$ --

At col. 18, line 38, delete "13 86 (P), 5 12" and substitute therefore -- 13.86 (P), 5.12 --

At col. 19, line 15, delete "8 98 (P')" and substitute therefore -- 8.98 (P) --

At col. 19, line 15, delete "22 9" and substitute therefore -- 22.9 --

UNITED STATES PATENT AND TRADEMARK OFFICE
CERTIFICATE OF CORRECTION

PATENT NO. : 5,376,649

DATED : December 27, 1994

INVENTOR(S) : Pohjala et al.

It is certified that error appears in the above-indentified patent and that said Letters Patent is hereby corrected as shown below:

At col. 19, line 45, delete "20 20" and substitute therefore -- 20.20 --

At col. 20, line 37, delete "2pp" and substitute therefore -- $^2J_{pp}$ --

At col. 24, line 51, delete "§ 11 50 (P), 9 36" and substitute therefore -- § 11.50 (P), 9.36 --

At col. 26, line 17, before "an" insert -- In --

At col. 26, line 29, delete "$^2J_{pp}$23.4" and substitute therefore -- $^2J_{pp}$ = 23.4

At col. 26, line 38, delete "mono," and substitute therefore -- mono- --

At col. 27, line 9, delete "6"

At col. 27, line 16, delete "CH3CN" and substitute therefore -- $CH_3CN$ --

At col. 27, line 35, delete "§ 6 11.86" and substitute therefore -- § 11.86 --

UNITED STATES PATENT AND TRADEMARK OFFICE
CERTIFICATE OF CORRECTION

PATENT NO. : 5,376,649

DATED : December 27, 1994

INVENTOR(S) : Pohjala et al.

It is certified that error appears in the above-indentified patent and that said Letters Patent is hereby corrected as shown below:

At col. 27, line 41, delete "$^2J = 16.7$" and substitute therefore -- $^2J_{pp} = 16.7$ --

At col. 27, line 44, delete "$(D_{20}O)$" and substitute therefore -- $(D_2O)$ --

At col. 28, line 50, after "$(CDCl_3)$: insert -- § --

At col. 28, line 53, delete "moles" and substitute therefore -- mmoles --

At col. 29, line 13, after "stereoisomers" insert -- and --

Signed and Sealed this

Twenty-fifth Day of April, 1995

Attest:

BRUCE LEHMAN

*Attesting Officer*     *Commissioner of Patents and Trademarks*